US008173792B2

(12) United States Patent
Wandless et al.

(10) Patent No.: US 8,173,792 B2
(45) Date of Patent: May 8, 2012

(54) METHOD FOR REGULATING PROTEIN FUNCTION IN CELLS USING SYNTHETIC SMALL MOLECULES

(75) Inventors: Thomas J. Wandless, Menlo Park, CA (US); Laura Anne Banaszynski, New York, NY (US); Mari Iwamoto, Stanford, CA (US); Lystranne Alysia Maynard, Silver Spring, MD (US); Ling-chun Chen, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 272 days.

(21) Appl. No.: 12/069,235

(22) Filed: Feb. 8, 2008

(65) Prior Publication Data

US 2009/0215169 A1 Aug. 27, 2009

Related U.S. Application Data

(60) Provisional application No. 60/900,552, filed on Feb. 9, 2007.

(51) Int. Cl.
*C07H 21/02* (2006.01)
*C12N 15/63* (2006.01)
*A01K 67/00* (2006.01)

(52) U.S. Cl. ...................... 536/23.4; 435/455

(58) Field of Classification Search .................. None
See application file for complete search history.

(56) References Cited

U.S. PATENT DOCUMENTS

| 4,442,203 | A | 4/1984 | Varshavsky |
|---|---|---|---|
| 5,071,775 | A | 12/1991 | Snapka et al. |
| 5,093,242 | A | 3/1992 | Bachmair et al. |
| 5,122,463 | A | 6/1992 | Varshavsky et al. |
| 5,132,213 | A | 7/1992 | Bachmair et al. |
| 5,196,321 | A | 3/1993 | Bachmair et al. |
| 5,212,058 | A | 5/1993 | Baker et al. |
| 5,391,490 | A | 2/1995 | Varshavsky et al. |
| 5,494,818 | A | 2/1996 | Baker et al. |
| 5,503,977 | A | 4/1996 | Johnsson et al. |
| 5,538,862 | A | 7/1996 | Wu et al. |
| 5,763,212 | A | 6/1998 | Varshavsky et al. |
| 5,766,927 | A | 6/1998 | Baker et al. |
| 6,133,456 | A | 10/2000 | Holt et al. |
| 6,150,527 | A * | 11/2000 | Holt et al. ............... 546/189 |
| 6,159,732 | A | 12/2000 | Varshavsky et al. |
| 2002/0100068 | A1 | 7/2002 | Chambon et al. |
| 2004/0038373 | A1 | 2/2004 | Platz et al. |
| 2005/0214738 | A1* | 9/2005 | Stankunas et al. ........... 435/4 |

OTHER PUBLICATIONS

Banaszynski et al. A rapid, reversible, and tunable method to regulate protein function in living cells using synthetic small molecules. Cell 126:995-1004, Sep. 2006.*
Banaszynski et al. Conditional control of protein function. Chemistry & Biology 13:11-21, Jan. 2006.*
Clackson, T. A stability switch for proteins. Chemistry & Biology 13:926-928, 2006.*
Armstrong, C.M. and Goldberg, D.E., *Nature Methods*, 4(12):1007-1009 (2007).
Bishop, A.C. et al., *Current Biology*, 8(5):257-266 (1998).
Choi, J. et al., Science, 273:239-241 (1996).
Clackson, T. et al., *Proc. Natl. Acad. Sci. U.S.A.*, 95:10437-10442 (1998).
Herm-Gotz et al., *Nature Methods*, 4(12):1003-1009 (2007).
Holt, D.A. et al., *J. Am. Chem. Soc.*, 115:9925-9938 (1993).
Iuliucci, J.D. et al., *J. Clin. Pharmacol.*, 41:870-879 (2001).
Liberles, S.D. et al., *Proc. Natl. Acad. Sci. U.S.A.*, 94:7825-7830 (1997).
Pollock, R. and Clackson, T., *Current. Opinion in Biotechnology*, 13:459-467 (2002).
Shah, K. et al., *Proc. Natl. Acad. Sci. U.S.A.*, 94:3565-3570 (1997).
Striepen, Boris, *Nature Methods*, 4(12):999-1000 (2007).
Vilella-Bach, M. et al., *J. Biol. Chem.*, 274(7):4266-72 (1999).
Yana, W. et al., *J. Med Chem.*, 43:1135-42 2000.
Foa, et al., "IL2 treatment for cancer: from biology to gene therapy", British J. Cancer, vol. 66, No. 6, pp. 992-998 (1992).
Kaufman, et al., "Local delivery of vaccinia virus expressing multiple costimulatory molecules for the treatment of established tumors", Human Gene Therapy, vol. 17, No. 2, pp. 239-244 (2006).
La Porta and Comolli, "Biochemical and immunological characterization of calcium-dependent and -independent PKC isoenzymes in renal ischemia", Biochemical and Biophysical Research Communications, vol. 191, No. 3, pp. 1124-1130 (1993).
McCart, et al., "Systematic cancer therapy with a tumor-selective vaccinia virus mutant lacking thymidine kinase and vaccinia growth factor genes", Cancer Res., vol. 61, No. 24, pp. 8751-8757 (2001).
Payne and Smeda, "Cerebrovacular alterations in pressure and protein kinase C-mediated constriction in Dahl salt-sensitive rats", J. Hypertension, vol. 20, No. 7, pp. 1355-1363 (2002).
Raval, et al., "Protein kinase C delta cleavage initiates an aberrant signal transduction pathway after cardiac arrest and oxygen glucose deprivation", J. Cerebral Blood Flow & Metab., vol. 25, No. 6, pp. 730-741 (2005).
Rosengren, et al., "Enhanced blood-brain barrier leakage to evans blue-labeled albumin after air embolism in ethanol-intoxicated rats", ACTA Neuropath., vol. 38, No. 2, pp. 149-152 (1977).
Stanimirovic, et al., "Angiotensin II-induced fluid phase endocytosis in human cerebrovascular endothelial cells is regulated by the inositol-phosphate signaling pathway", J. Cell. Physiol., vol. 169, No. 3, pp. 455-467 (1996).
Thorn, et al., "Synergistic antitumor effects of immune cell-viral biotherapy", Science, vol. 311, pp. 1780-1784 (2006).
Werber and Fitch-Burke, "Effect of chronic hypertension on acute hypertensice disruption of the blood-brain barrier in rats", Hypertension, vol. 12, No. 6, pp. 549-555 (1988).
Dohmen et al., "Heat-inducible degron: a method for constructing temperature-sensitive mutants", Science, vol. 253, pp. 1273-1276 (1994).
Johnston et al., "Methoirexate inhibits proteolysis of dihydrofolate reductase by the N-end rule pathway", J. Biol. Chem., vol. 270, No. 14, pp. 8172-8175 (1996).
Levy et al., "Analysis of a conditional degradation signal in yeast and mammalian cells", Eur. J. Biochem., vol. 259, pp. 244-252 (1999).

* cited by examiner

*Primary Examiner* — Quang Nguyen

(74) *Attorney, Agent, or Firm* — Judy M. Mohr; Stephen Todd; King & Spalding LLP

(57) ABSTRACT

Methods and compositions for the rapid and reversible destabilizing of specific proteins using cell-permeable, synthetic molecules are described. Stability-affecting proteins, e.g., derived from FKBP and DHFR proteins are fused to a protein of interest and the presence or absence of the ligand is used to modulate the stability of the fusion protein.

3 Claims, 23 Drawing Sheets

A

B

SEQ ID NO: 1
FKBP F36V

GVQVETISPG DGRTFPKRGQ TCVVHYTGML EDGKK<u>V</u>DSSR DRNKPFKFML 50
GKQEVIRGWE EGVAQMSVGQ RAKLTISPDY AYGATGHPGI IPPHATLVFD 100
VELLKLE 107

SEQ ID NO: 2
FKBP F15S

GVQVETISPG DGRT<u>S</u>PKRGQ TCVVHYTGML EDGKKFDSSR DRNKPFKFML 50
GKQEVIRGWE EGVAQMSVGQ RAKLTISPDY AYGATGHPGI IPPHATLVFD 100
VELLKLE 107

SEQ ID NO: 3
FKBP V24A

GVQVETISPG DGRTFPKRGQ TCV<u>A</u>HYTGML EDGKKFDSSR DRNKPFKFML 50
GKQEVIRGWE EGVAQMSVGQ RAKLTISPDY AYGATGHPGI IPPHATLVFD 100
VELLKLE 107

SEQ ID NO: 4
FKBP H25R

GVQVETISPG DGRTFPKRGQ TCVV<u>R</u>YTGML EDGKKFDSSR DRNKPFKFML 50
GKQEVIRGWE EGVAQMSVGQ RAKLTISPDY AYGATGHPGI IPPHATLVFD 100
VELLKLE 107

SEQ ID NO: 5
FKBP E60G

GVQVETISPG DGRTFPKRGQ TCVVHYTGML EDGKKFDSSR DRNKPFKFML 50
GKQEVIRGW<u>G</u> EGVAQMSVGQ RAKLTISPDY AYGATGHPGI IPPHATLVFD 100
VELLKLE 107

SEQ ID NO: 6
FKBP L106P

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFD 100
VELLK<u>P</u>E 107

FIG. 21A

SEQ ID NO: 7
FKBP D100G

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFG 100
VELLKLE 107

SEQ ID NO: 8
FKBP M66T

GVQVETISPG DGRTFPKRGQ TCVVHYTGML EDGKKFDSSR DRNKPFKFML 50
GKQEVIRGWE EGVAQTSVGQ RAKLTISPDY AYGATGHPGI IPPHATLVFD 100
VELLKLE 107

SEQ ID NO: 9
FKBP R71G

GVQVETISPG DGRTFPKRGQ TCVVHYTGML EDGKKFDSSR DRNKPFKFML 50
GKQEVIRGWE EGVAQMSVGQ GAKLTISPDY AYGATGHPGI IPPHATLVFD 100
VELLKLE 107

SEQ ID NO: 10
FKBP D100N

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFN 100
VELLKLE 107

SEQ ID NO: 11
FKBP E102G

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFD 100
VGLLKLE 107

SEQ ID NO: 12
FKBP K105I

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFD 100
VELLILE 107

FIG. 21B

SEQ ID NO: 13
DHFR

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVY 100
EQFLPKAQKL YLTHIDAEVE GDTHFPDYEP DDWESVFSEF HDADAQNSHS 150
YCFEILERR 159

SEQ ID NO: 14
DHFR Y100I

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVI 100
EQFLPKAQKL YLTHIDAEVE GDTHFPDYEP DDWESVFSEF HDADAQNSHS 150
YCFEILERR 159

SEQ ID NO: 15
DHFR G121V

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVY 100
EQFLPKAQKL YLTHIDAEVE VDTHFPDYEP DDWESVFSEF HDADAQNSHS 150
YCFEILERR 159

SEQ ID NO: 16
DHFR F103L

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVY 100
EQLLPKAQKL YLTHIDAEVE GDTHFPDYEP DDWESVFSEF HDADAQNSHS 150
YCFEILERR 159

SEQ ID NO: 17
DHFR N18T A19V

MISLIAALAV DHVIGMETVM PWNLPADLAW FKRNTLNKPV IMGRHTWESI 50
GRPLPGRKNI ILSSQPSTDD RVTWVKSVDE AIAACGDVPE IMVIGGGRVY 100
EQFLPKAQKL YLTHIDAEVE GDTHFPDYEP DDWESVFSEF HDADAQNSHS 150
YCFEILERR 159

SEQ ID NO: 18
Diversity Sequence

TRGVEEVAEGVVLLRRRGN

FIG. 21C

SEQ ID NO: 19
H12Y/Y100I

MISLIAAAV DYVIGMENAM PWNLPADLAW FKRNTLNKPV IMGRHTWESI 50
GRPLPGRKNI ILSSQPSTDD RVTWVKSVDE AIAACGDVPE IMVIGGGRVI 100
EQFLPKAQKL YLTHIDAEVE GDTHFPDYEP DDWESVFSEF HDADAQNSHS 150
YCFEILERR 159

SEQ ID NO: 20
H12L/Y100I

MISLIAAAV DLVIGMENAM PWNLPADLAW FKRNTLNKPV IMGRHTWESI 50
GRPLPGRKNI ILSSQPSTDD RVTWVKSVDE AIAACGDVPE IMVIGGGRVI 100
EQFLPKAQKL YLTHIDAEVE GDTHFPDYEP DDWESVFSEF HDADAQNSHS 150
YCFEILERR 159

SEQ ID NO: 21
R98H/F103S

MISLIAAAV DHVIGMENAM PWNLPADLAW FKRNTLNKPV IMGRHTWESI 50
GRPLPGRKNI ILSSQPSTDD RVTWVKSVDE AIAACGDVPE IMVIGGGHVY 100
EQSLPKAQKL YLTHIDAEVE GDTHFPDYEP DDWESVFSEF HDADAQNSHS 150
YCFEILERR 159

SEQ ID NO: 22
M42T/H114R

MISLIAAAV DHVIGMENAM PWNLPADLAW FKRNTLNKPV ITGRHTWESI 50
GRPLPGRKNI ILSSQPSTDD RVTWVKSVDE AIAACGDVPE IMVIGGGRVY 100
EQFLPKAQKL YLTRIDAEVE GDTHFPDYEP DDWESVFSEF HDADAQNSHS 150
YCFEILERR 159

SEQ ID NO: 23
I61F/T68S

MISLIAAAV DHVIGMENAM PWNLPADLAW FKRNTLNKPV IMGRHTWESI 50
GRPLPGRKNI FLSSQPSSDD RVTWVKSVDE AIAACGDVPE IMVIGGGRVY 100
EQFLPKAQKL YLTHIDAEVE GDTHFPDYEP DDWESVFSEF HDADAQNSHS 150
YCFEILERR 159

FIG. 21D

SEQUENCE LISTING

<160> NUMBER OF SEQ ID NOS: 23

<210> SEQ ID NO 1
<211> LENGTH: 107
<212> TYPE: PRT
<213> ORGANISM: Artificial Sequence
<220> FEATURE:
<223> OTHER INFORMATION: FKBP F36V peptide

<400> SEQUENCE: 1

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

```
Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 2
<211> LENGTH: 107
<212> TYPE: PRT
<213> ORGANISM: Artificial Sequence
<220> FEATURE:
<223> OTHER INFORMATION: FKBP F15S peptide

<400> SEQUENCE: 2

```
Gly Val Gln Val Glu Thr Ile Ser Pro Gly Asp Gly Arg Thr Ser Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 3
<211> LENGTH: 107
<212> TYPE: PRT
<213> ORGANISM: Artificial Sequence
<220> FEATURE:
<223> OTHER INFORMATION: FKBP V24A peptide

<400> SEQUENCE: 3

```
Gly Val Gln Val Glu Thr Ile Ser Pro Gly Asp Gly Arg Thr Phe Pro
1               5                   10                  15

Lys Arg Gly Gln Thr Cys Val Ala His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 4
<211> LENGTH: 107
<212> TYPE: PRT
<213> ORGANISM: Artificial Sequence

```
<220> FEATURE:
<223> OTHER INFORMATION: FKBP H25R peptide

<400> SEQUENCE: 4

Gly Val Gln Val Glu Thr Ile Ser Pro Gly Asp Gly Arg Thr Phe Pro
1               5                   10                  15

Lys Arg Gly Gln Thr Cys Val Val Arg Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 5
<211> LENGTH: 107
<212> TYPE: PRT
<213> ORGANISM: Artificial Sequence
<220> FEATURE:
<223> OTHER INFORMATION: FKBP E60G peptide

<400> SEQUENCE: 5

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Gly Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 6
<211> LENGTH: 107
<212> TYPE: PRT
<213> ORGANISM: Artificial Sequence
<220> FEATURE:
<223> OTHER INFORMATION: FKBP L106P peptide

<400> SEQUENCE: 6

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
```

```
                65                  70                  75                  80
Ala Tyr Gly Ala Thr Gly His Pro Gly Ile Ile Pro Pro His Ala Thr
                    85                  90                  95

Leu Val Phe Asp Val Glu Leu Leu Lys Pro Glu
                100                 105

<210> SEQ ID NO 7
<211> LENGTH: 107
<212> TYPE: PRT
<213> ORGANISM: Artificial Sequence
<220> FEATURE:
<223> OTHER INFORMATION: FKBP D100G peptide

<400> SEQUENCE: 7

Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                    85                  90                  95

Leu Val Phe Gly Val Glu Leu Leu Lys Leu Glu
                100                 105

<210> SEQ ID NO 8
<211> LENGTH: 107
<212> TYPE: PRT
<213> ORGANISM: Artificial Sequence
<220> FEATURE:
<223> OTHER INFORMATION: FKBP M66T peptide

<400> SEQUENCE: 8

Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Thr Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                    85                  90                  95

Leu Val Phe Asp Val Glu Leu Leu Lys Leu Glu
                100                 105

<210> SEQ ID NO 9
<211> LENGTH: 107
<212> TYPE: PRT
<213> ORGANISM: Artificial Sequence
<220> FEATURE:
<223> OTHER INFORMATION: FKBP R71G peptide

<400> SEQUENCE: 9
```

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Gly Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 10
<211> LENGTH: 107
<212> TYPE: PRT
<213> ORGANISM: Artificial Sequence
<220> FEATURE:
<223> OTHER INFORMATION: FKBP D100N peptide

<400> SEQUENCE: 10

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asn Val Glu Leu Leu Lys Leu Glu
            100                 105

<210> SEQ ID NO 11
<211> LENGTH: 107
<212> TYPE: PRT
<213> ORGANISM: Artificial Sequence
<220> FEATURE:
<223> OTHER INFORMATION: FKBP E102G peptide

<400> SEQUENCE: 11

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95
```

```
Leu Val Phe Asp Val Gly Leu Leu Lys Leu Glu
                100                 105
```

<210> SEQ ID NO 12
<211> LENGTH: 107
<212> TYPE: PRT
<213> ORGANISM: Artificial Sequence
<220> FEATURE:
<223> OTHER INFORMATION: FKBP K105I peptide

<400> SEQUENCE: 12

```
Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Ile Leu Glu
                100                 105
```

<210> SEQ ID NO 13
<211> LENGTH: 159
<212> TYPE: PRT
<213> ORGANISM: Artificial Sequence
<220> FEATURE:
<223> OTHER INFORMATION: DHFR peptide

<400> SEQUENCE: 13

```
Met Ile Ser Leu Ile Ala Ala Leu Ala Val Asp His Val Ile Gly Met
 1               5                  10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
                100                 105                 110

Thr His Ile Asp Ala Glu Val Glu Gly Asp Thr His Phe Pro Asp Tyr
            115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155
```

<210> SEQ ID NO 14
<211> LENGTH: 159
<212> TYPE: PRT
<213> ORGANISM: Artificial Sequence
<220> FEATURE:

<223> OTHER INFORMATION: DHFR Y100I peptide

<400> SEQUENCE: 14

```
Met Ile Ser Leu Ile Ala Ala Leu Ala Val Asp His Val Ile Gly Met
 1               5                  10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
        50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 15
<211> LENGTH: 159
<212> TYPE: PRT
<213> ORGANISM: Artificial Sequence
<220> FEATURE:
<223> OTHER INFORMATION: DHFR G121V peptide

<400> SEQUENCE: 15

```
Met Ile Ser Leu Ile Ala Ala Leu Ala Val Asp His Val Ile Gly Met
 1               5                  10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
        50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Val Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 16
<211> LENGTH: 159
<212> TYPE: PRT
<213> ORGANISM: Artificial Sequence
<220> FEATURE:

<223> OTHER INFORMATION: DHFR F103L peptide

<400> SEQUENCE: 16

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Leu Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 17
<211> LENGTH: 159
<212> TYPE: PRT
<213> ORGANISM: Artificial Sequence
<220> FEATURE:
<223> OTHER INFORMATION: DHFR N18T A19V

<400> SEQUENCE: 17

Met Ile Ser Leu Ile Ala Ala Leu Ala Val Asp His Val Ile Gly Met
1               5                   10                  15

Glu Thr Val Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 18
<211> LENGTH: 19
<212> TYPE: PRT
<213> ORGANISM: Artificial Sequence
<220> FEATURE:

-continued

<223> OTHER INFORMATION: Diversity sequence peptide

<400> SEQUENCE: 18

Thr Arg Gly Val Glu Glu Val Ala Glu Gly Val Val Leu Leu Arg Arg
1               5                   10                  15

Arg Gly Asn

<210> SEQ ID NO 19
<211> LENGTH: 159
<212> TYPE: PRT
<213> ORGANISM: Artificial Sequence
<220> FEATURE:
<223> OTHER INFORMATION: DHFR H12Y/Y100I peptide

<400> SEQUENCE: 19

Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 20
<211> LENGTH: 159
<212> TYPE: PRT
<213> ORGANISM: Artificial Sequence
<220> FEATURE:
<223> OTHER INFORMATION: DHFR H12L/Y100I peptide

<400> SEQUENCE: 20

Met Ile Ser Leu Ile Ala Ala Leu Ala Val Asp Leu Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
            115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155

<210> SEQ ID NO 21
<211> LENGTH: 159
<212> TYPE: PRT
<213> ORGANISM: Artificial Sequence
<220> FEATURE:
<223> OTHER INFORMATION: DHFR R98H/F103S peptide

<400> SEQUENCE: 21

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly His Val Tyr Glu Gln Ser Leu Pro Lys Ala Gln Lys Leu Tyr Leu
            100                 105                 110

Thr His Ile Asp Ala Glu Val Glu Gly Asp Thr His Phe Pro Asp Tyr
            115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155

<210> SEQ ID NO 22
<211> LENGTH: 159
<212> TYPE: PRT
<213> ORGANISM: Artificial Sequence
<220> FEATURE:
<223> OTHER INFORMATION: DHFR M42T/H114R peptide

<400> SEQUENCE: 22

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Thr Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

```
Thr Arg Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155

<210> SEQ ID NO 23
<211> LENGTH: 159
<212> TYPE: PRT
<213> ORGANISM: Artificial Sequence
<220> FEATURE:
<223> OTHER INFORMATION: DHFR I61F/T68S peptide

<400> SEQUENCE: 23

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Phe Leu Ser Ser
        50                  55                  60

Gln Pro Ser Ser Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155
```

METHOD FOR REGULATING PROTEIN FUNCTION IN CELLS USING SYNTHETIC SMALL MOLECULES

PRIORITY

The application claims the benefit of U.S. Provisional Application No. 60/900,552, filed Feb. 9, 2007, incorporated herein by reference in its entirety.

STATEMENT REGARDING GOVERNMENT INTEREST

This work was supported in part by National Institutes of Health grants (GM068589 and GM073046). Accordingly, the United States government has certain rights in this invention.

TECHNICAL FIELD

Compositions, systems, and methods for modulating the stability of proteins using cell-permeable small molecules are described. Proteins of interest are fused to a stability-affecting variant protein derived from a naturally-occurring protein capable of interacting with a small-molecule ligand. The presence of absence of the ligand in a cell modulates the stability of the fusion protein.

BACKGROUND

Techniques that target gene function at the level of DNA and mRNA provide powerful methods for modulating the expression of proteins encoded by specific genes. For example, the tet/dox and Cre/lox systems have been widely used to target gene expression at the transcriptional level (Ryding et al., 2001) and RNA interference is rapidly being adopted as a method to achieve post-transcriptional gene silencing (Fire et al., 1998; Madema, 2004).

However, methods for regulating protein function directly are limited, especially in mammalian cells. Inhibitors or activators of particular proteins have been identified, and often take the form of cell-permeable small molecules. Many of these molecules have found widespread use as biological probes, often because the speed, dosage-dependence, and reversibility of their activities, which complement methods for genetically modulating gene expression (Schreiber, 2003). However these inhibitors or activators are often promiscuous, affecting several proteins rather than a specific protein (Davies et al, 2000; Bain et al., 2003; Godl et al., 2003).

Shokat and coworkers have developed a method by which specific kinases can be inhibited using a small-molecule modulator (Shah et al., 1997; Bishop et al., 1998). This method involves mutating the protein of interest, typically replacing a large conserved residue in the active site with a smaller residue, such as glycine or alanine. Specificity is achieved by chemically modifying a promiscuous inhibitor to include a bulky side-chain substituent (e.g., R-group), which fills the corresponding cavity in the binding site of the modified protein of interest, while preventing productive interactions with other kinases. While this so-called "bump-hole" approach has been successful both in cultured cells and in mice (Bishop et al., 2000; Wang et al., 2003, Chen et al., 2005), it appears to be limited to ATPases and GTPases. Additional methods are required to probe the function of a wider variety of proteins.

Other investigators have devised alternative strategies to perturb protein function by exploiting existing cellular processes (Banaszynski and Wandless, 2006). For example, Varshavsky and coworkers developed methods for controlling protein function based on the importance of certain N-terminal residues for protein stability (Bachmair et al., 1986). Szostak and coworkers showed that a small peptide sequence could be fused to the N-terminus of a protein of interest to modulate protein stability (Park et al., 1992). Varshavsky and coworkers have further isolated a temperature-sensitive peptide sequence that greatly reduced the half-life or dihydrofolate reductase (DHFR) at the non-permissive temperatures (Dohmen et al., 1994). This approach has been used to study proteins in yeast (Labib et al., 2000; Kanemaki et al., 2003). More recently, several researchers have engineered systems in which dimeric small molecules are used to conditionally target fusion proteins for degradation via E3 ligase or the proteasome, itself (Schneekloth et al., 2004; Janse et al., 2004). However, these systems require either a prior knowledge of the high-affinity ligands that modulate the activity of a protein of interest or they are restricted to genetically engineered yeast strains.

An alternative approach for controlling protein function directly is to interfere with subcellular localization. Several methods are available to regulate protein localization using small-molecule by taking advantage of the FKBP-rapamycin-FRB ternary complex (Kohler and Bertozzi, 2003 and Inoue et al., 2005). Rapamycin and FK506 are potent, commercially available immunosuppressive agents, which are ligands of the FK506-binding protein (FKBP12, FKBP). Rapamycin also binds to FKBP-rapamycin-associated protein (FRAP). FRAP is also called the mammalian target of rapamycin (mTOR), rapamycin and FKBP target 1 (RAFT1), and FRB. Rapamycin binds to and inhibits mTOR by interacting with its FKBP-rapamycin-binding (FRB) domain to inhibit/delay G1 cell cycle progression in mammalian cells (see, e.g., Choi, J. et al. (1996) Science 273:239-42 and Vilella-Bach, M. et al. (1999) J. Biol. Chem. 274:4266-72. The FKBP-rapamycin-binding domain is required for FKBP-rapamycin-associated protein kinase activity and G1 progression. Fusions of proteins of interest can be made to either FKBP or the FRP domain of FRAP/mTOR. Colocalization of the protein of interest is induced upon addition of rapamycin.

Because rapamycin has inherent biological activity, researchers have developed a "bump-hole" strategy (similar to that employed by Shokat and coworkers), wherein rapamycin derivatives possessing large substituents at the FRB binding interface bind poorly to wild-type FRB and in turn the biologically relevant target FRAP/mTOR, with binding restored upon introduction of compensatory cavity-forming mutations in FRB. Specifically, a C20-methallyl-rapamycin derivative (MaRap) binds to a triple-mutated variant of FRB called FRB* (Liberles et al., 1997).

While these methods for regulating protein function directly are noteworthy, there has yet to be described a convenient, general method for regulating protein function, particularly a method that does not require the interaction of multiple proteins. Improved methods for regulating protein function directly, particularly in mammalian cells, are needed.

REFERENCES

The following references, and any other references cited in the text, are hereby incorporated by reference in their entirety.
Bachmair, A. et al. (1986). *Science* 234:179-186.
Bain, J. et al. (2003) *Biochem. J.* 371:199-204.
Banaszynski, L. A. et al. (2006) *Chem. Biol.* 13:11-21.
Bence, N. F. et al. (2001). *Science* 292:1552-1555.

Bishop, A. C. et al. (1998) *Current Biology* 8:257-266.
Bishop, A. C. et al. (2000) *Nature* 407:395-401.
Chen, X. et al. (2005) Neuron 46:13-21.
Clackson, T. et al. (1998) *Proc. Natl. Acad. Sci. U.S.A.* 95:10437-10442.
Corish, P. and Tyler-Smith, C. (1999) *Protein Eng.* 12:1035-1040.
Davies, S. P. et al. (2000) *Biochem. J.* 351:95-105.
Dohmen, R. J. et al. (1994) *Science* 263:1273-1276.
Elbashir, S. M. et al. (2001) *Nature* 411:494-498.
Fire, A. et al. (1998) *Nature* 391:806-811.
Godl, K. et al. (2003) *Proc. Natl. Acad. Sci. U.S.A.* 100: 15434-15439.
Heo, W. D. and Meyer, T. (2003) *Cell* 113:315-328.
Hicke, L. and Dunn, R. (2003) *Annu. Rev. Cell Dev. Biol.* 19:141-172.
Inoue, T. et al. (2005) *Nature Methods* 2:415-418.
Iuliucci, J. D. et al. (2001) *J. Clin. Pharmacol.* 41:870-879.
Janse, D. M. et al. (2004) *J. Biol. Chem.* 279:21415-21420.
Kanemaki, M. et al. (2003) *Nature* 423:720-724.
Kohler, J. J. and Bertozzi, C. R. (2003) *Chem. Biol.* 10:1303-1331.
Labib, K. et al. (2000) *Science* 288:1643-1646.
Liberles, S. D. et al. (1997) *Proc. Natl. Acad. Sci. U.S.A.* 94:7825-7830.
Mayer, T. T. et al. (1999) *Science,* 286:971-974.
Medema, R. H. (2004) *Biochem. J.* 380:593-603.
Nigg, E. A. (2001) Nature Rev. Mol. Cell. Biol. 2:21-32.
Niwa, H. et al. (2000) *Nature Genetics* 24:372-376.
Pan, X. et al. (2005) *J. Biol. Chem.* 280:22385-22394.
Park, E-C. et al. (1992) *Proc. Natl. Acad. Sci. U.S.A.* 89:1249-1252.
Pickart, C. M. (2004) *Cell* 116:181-190.
Pollock, R. and Clackson, T. (2002) *Curr. Opin. Biotechnol.* 13:459-467.
Raab, R. M. and Stephanopoulos, G. (2004) *Biotechnology & Bioengineering* 88:121-132.
Ryding, A. D. S. et al. (2001) *J. Endocrinol.* 171:1-14.
Schneekloth, J. S. et al. (2004) *J. Am. Chem. Soc.* 126:3748-3754.
Schreiber, S. L. (2003) *Chem. & Eng. News* 81:51-61.
Shah, K. et al. (1997) *Proc. Natl. Acad. Sci. U.S.A.* 94:3565-3570.
Stankunas, K. et al. (2003) Mol. Cell. 12:1615-1624.
Tan, D. S. (2005) *Nature Chem. Biol.* 1:74-84.
Wang, H. et al. (2003) *Proc. Natl. Acad. Sci. U.S.A.* 100:4287-4292.
Zaccolo, M. et al. (1996) *J. Mol. Biol.* 255:589-603.
Choi, J. et al. (1996) *Science* 273:239-42.
Vilella-Bach, M. et al. (1999) *J. Biol. Chem.* 274:4266-72.
Lin, A. H. et al. (2005) *J. Immunol.* 175:547-54.
Luo, J. et al. (2006) *Proc. Nat'l. Acad. Sci. USA* 103:18326-31.

BRIEF SUMMARY

Compositions, systems, and methods for modulating the stability of proteins using cell-permeable small molecules are described. Proteins of interest are fused to a stability-affecting protein capable of interacting with a small-molecule ligand, the presence, absence, or amount of which is used to modulate the stability of the fusion protein.

In one aspect, a conditional protein stability system is provided, comprising:
a nucleic acid sequence encoding a fusion protein that includes
a protein of interest fused in-frame to
a single-polypeptide chain, ligand-dependent, stability-affecting protein that is derived from a naturally-occurring ligand binding protein, and
a ligand that binds to the stability-affecting protein to modulate its stability, wherein upon introduction of the nucleic acid sequence to a cell,
the fusion protein is expressed and
the stability of the fusion protein can be modulated by amount of ligand present in the cells.

In some embodiments, the stability-affecting protein destabilizes the protein of interest in the absence of the ligand and stabilizes the protein in the presence of the ligand.

In some embodiments, the stability-affecting protein stabilizes the protein of interest in the absence of the ligand and destabilizes the protein in the presence of the ligand.

In some embodiments, the ligand preferentially binds to the stability-affecting protein compared to the naturally-occurring ligand-binding protein.

In some embodiments, the stability-affecting protein is a variant FKBP protein and the fusion protein is stabilized in the presence of a FKBP ligand. In particular embodiments, the variant FKBP protein has the substitution F36V.

In some embodiments, the variant FKBP protein comprises one or more amino acid substitutions selected from F15S, V24A, H25R, E60G, L106P, D100G, M66T, R71G, D100N, E102G, and K105I. In particular embodiments, the variant FKBP protein additionally has the substitution F36V.

In some embodiments, the FKBP ligand is Shield1.

In some embodiments, the stability-affecting protein is a variant FKBP and the fusion protein is destabilized in the presence of a FKBP ligand. In particular embodiments, the variant FKBP includes a C-terminal extension of amino acids substantially identical to that of sequence of SEQ ID NO: 18. In particular embodiments, the variant FKBP includes the substitution F36V.

In some embodiments, the naturally-occurring ligand binding protein is DHFR and the fusion protein is stabilized in the presence of a DHFR ligand.

In some embodiments, the variant DHFR protein has one or more substitutions selected from G121V and Y100I and the stability-affecting protein is located at the N-terminus or C-terminus of the protein of interest.

In some embodiments, the variant DHFR protein has one or more substitutions selected from N18T/A19V and F103L and the stability-affecting protein is located at the C-terminus of the protein of interest.

In some embodiments, the variant DHFR protein comprises one or more amino acid substitutions selected from H12Y/Y100I, H12L/Y100I, R98H/F103S, M42T/H114R, and I61F/T68S and the stability-affecting protein is located at the N-terminus of the protein of interest.

In some embodiments, the DHFR ligand is trimethoprim (TMP).

In another aspect, a FKBP variant is provided having one or more amino acid substitutions selected from F15S, V24A, H25R, E60G, L106P, D100G, M66T, R71G, D100N, E102G, and K105I. In particular embodiments, the variant further has the substitution F36V.

In another aspect, a FKBP variant destabilized by the presence of ligand is provided. In particular embodiments, the amino acid extension has a sequence that is substantially identical to that of SEQ ID NO: 18. In particular embodiments, the variant further has the substitution F36V.

In another aspect, a DHFR variant is provided, having one or more amino acid substitutions selected from N18T/A19V, F103L, Y100I, G121V, H12Y/Y100I, H12L/Y100I, R98H/F103S, M42T/H114R, and I61F/T68S.

In another aspect, cells comprising nucleic acids encoding a fusion protein comprising a protein of interest fused in frame to a stability-affecting protein are provided. The cells may be in culture or in vivo.

In another aspect, a kit of parts is provided, comprising any of these systems.

In another aspect, a method for conditionally stabilizing a protein of interest (POI) is provided, comprising:

(a) fusing a nucleic acid encoding the POI in-frame to a nucleic acid encoding a variant ligand-binding protein to produce a nucleic acid encoding a fusion protein comprising the variant ligand-binding protein, (b) introducing the a nucleic acid encoding the fusion protein into a cell, (c) expressing the fusion protein is the cell, and (d) conditionally stabilizing the fusion protein in the presence or absence of the ligand.

In addition to the exemplary aspects and embodiments described above, further aspects and embodiments will become apparent by reference to the drawings and by study of the following descriptions.

BRIEF DESCRIPTION OF THE DRAWINGS

(FIG. 1A) A genetic fusion of a destabilizing domain (DD) to a protein of interest (POI) results in degradation of the entire fusion protein. Addition of a ligand for the destabilizing domain protects the fusion protein from degradation. (FIG. 1B) Synthetic ligands SLF* and Shield1 for FKBP F36V.

(FIG. 2A) Fluorescence of FKBP-YFP fusion proteins expressed in NIH3T3 cells as determined by flow cytometry in the absence of Shield1. (FIG. 2B) NIH3T3 cells stably expressing FKBP-YFP fusion proteins were treated with three-fold dilutions of Shield1 (1 μM to 0.1 nM) and the fluorescence was monitored by flow cytometry. (FIG. 2C) NIH3T3 cells stably expressing FKBP-YFP fusion proteins were either mock-treated (circles) or treated with 30 nM Shield1 (squares), 100 nM Shield1 (diamonds), 300 nM Shield1 (crosses), or 1 μM Shield1 (triangles). Fluorescence was monitored over time using flow cytometry. MFI was normalized to 100% of cells treated with 1 μM Shield1 at 24 hrs. (FIG. 2D) NIH3T3 cells stably expressing FKBP-YFP fusion proteins were treated with 1 μM Shield1 for 24 hours at which point the cells were washed with media to remove Shield1, and the decrease in fluorescence was monitored using flow cytometry.

(FIG. 2E) FKBP-YFP fusion proteins were either mock-treated or treated with 1 μM Shield1 for 24 hrs then subjected to immunoblot analysis with an anti-FKBP antibody. (FIG. 2F) NIH3T3 cells stably expressing F15S-YFP and L106P-YFP were treated with 1 μM Shield1 for 24 hrs. The cells were then washed with media and treated with 10 μM MG132 in the presence or absence of 1 μM Shield1 for 4 hrs. Immunoblot analysis was performed using an anti-YFP antibody. (FIG. 2G) HeLa cells were transfected with siRNA against lamin A/C and monitored over time. The time required for the reduction of lamin A/C was compared to the time required for degradation of L106P-YFP upon removal of Shield1 from NIH3T3 cells stably expressing the fusion protein.

(FIG. 4A) FKBP variants F15S and L106P were fused to the N-termini of several different proteins and transduced into NIH3T3 cells. Cell populations stably expressing the fusions were then either mock-treated or treated with 1 μM Shield1, and cell lysates were subjected to immunoblot analysis using antibodies specific for the protein of interest. Endogenous proteins served as loading controls (when detected) and Hsp90 served as a loading control otherwise. (FIG. 4B) FKBP variants D100G and L106P were fused to the C-termini of several different proteins of interest and treated as above.

(FIG. 16A) Y100I and G121V mutants. (FIG. 16B) F103L and N18T/A19V mutants.

FIG. 21A-21D show a list of sequences referred to in the application.

DETAILED DESCRIPTION

1. Definitions

Figure 1:
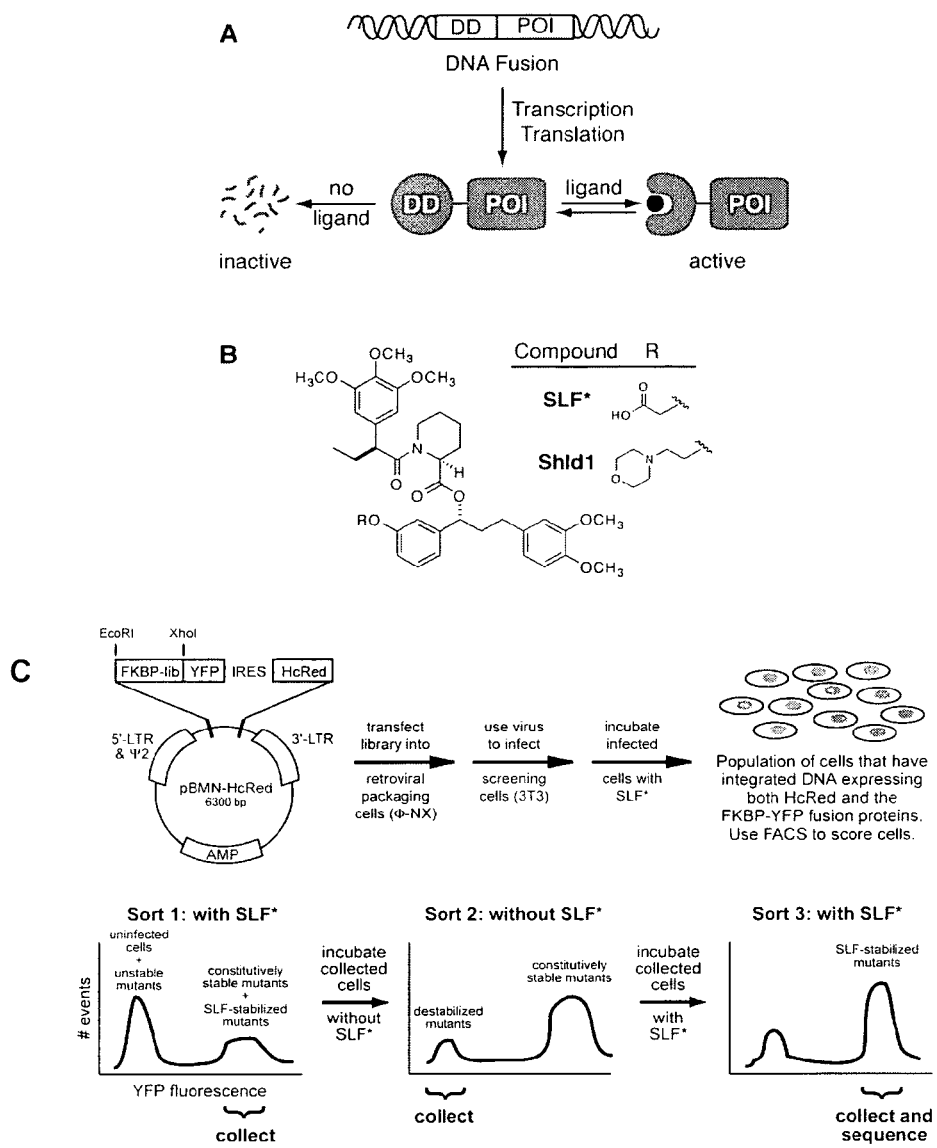
FIGS. 1A and 1B are diagrams illustrating a method for conditionally controlling protein stability.
FIG. 1C is a schematic illustrating the screening strategy described in the text.

As used herein, a "protein of interest" or "POI" is any protein, or functional fragment of derivative, thereof, that one skilled in the art wishes to study.

As used herein, "preferentially binds" means to bind with greater efficiency to a subject molecule (such as a particular amino acid sequence) than another molecule. The difference in binding efficiency may be 5-fold, 10-fold, 50-fold, 100-fold, 500-fold, 1,000-fold, 10,000 fold, or more.

As used herein, "introduction of nucleic to cells" means transfection, transduction (infection), or transformation of nucleic acids (e.g., DNA) into cells, such that the nucleic acids may be used by the cell to express a protein of interest.

As used herein, "degradation" or "destruction" of a protein means its hydrolysis into smaller proteins or amino acids, such as by the cellular proteosome.

"Rapamycin" is a naturally-occurring, small molecule immunosuppressant that is a ligand for FKBP.

"FKBP12" or "FKBP" is a 12 kDa protein that binds to the small-molecules rapamycin and FK506. The rapamycin-FKBP complexes can bind to the FRB domain of FRAP.

"FRAP," "mTOR," or "FRAP/mTOR" is a protein that binds, via its FRB domain, to rapamycin, or the FKBP-rapamycin complex.

A "FKBP variant" refers to a protein wherein one or more amino acid residues, e.g., at positions 15, 24, 25, 36, 60, 100, and 106, are substituted for an amino acid other than the amino acid in the FKBP F36V protein (SEQ ID NO: 1). Other amino acid positions that can be substituted are indicated in the Tables and Figures.

"FRB*" is a FRB variant with three point mutations, i.e., K2095P/T2098L/W2101F (using mTOR numbering), designed to bind rapamycin analogs such as MaRAP. Amino acid substitutions, or point mutations, are denoted herein, and in accord with conventional practice, as the old (original) residue in single-letter code, followed by its codon location, followed by the substitute (mutant) amino acid in single-letter code. For example, the F36V mutant of FKBP has Val in place of Phe at position 36 of the FKBP protein.

"MaRAP" is C20-methallylrapamycin, a synthetic rapamycin derivative that binds FRB* but not FRB.

"Shield1" is a synthetic small molecule that binds to wild-type FKBP, a FKBP variant having a F36V mutation/substitution, and likely other FKBP variants. Binding is about 1,000-fold tighter to the F36V variant compared to wild-type FKBP (Clackson, T. et al. (1998) *Proc. Natl. Acad. Sci. U.S.A.* 95:10437-10442).

As used herein, a "single-protein, ligand-dependent destabilization protein" or "single protein, stability-affecting protein" is a single polypeptide that functions as a ligand-dependent destabilization protein, as described herein. Such a destabilizing protein does not require the formation of a ternary complex, as is the case with the FKBP-rapamycin-FRB complex. A particular species is a "single-domain," ligand-dependent destabilization protein, wherein the single polypeptide comprises only a single domain (i.e., folded structure or functional unit as determined by X-ray crystallography, protease digestion, computer modeling, etc.

As used herein, "fused" means arranged in-frame as part of the same contiguous sequence of amino acids in a polypeptide. Fusion can be direct such there are no additional amino acid residues or via a linker to improve performance or add functionality.

As used herein, a "conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

As used herein, the terms "domain" and "region" are used interchangeably herein and refer to a contiguous sequence of amino acids within a POI or destabilizing domain, typically characterized by being either conserved or variable and having a defined function, such as ligand binding, conferring stability or instability, enzymatic function, etc.

As used herein, the terms "protein" and "polypeptide" are used interchangeably and without distinction to refer to a compound made up of a chain of amino acid residues linked by peptide bonds. Unless otherwise indicated, the sequence for peptides is given in the order from the "N" (or amino) terminus to the "C" (or carboxyl) terminus. It is understood that polypeptides include a contiguous sequence of amino acid residues.

A peptide or peptide fragment is "derived from" a parent peptide or polypeptide if it has an amino acid sequence that is homologous to, but not identical to, the parent peptide or polypeptide, or of a conserved fragment from the parent peptide or polypeptide.

Two amino acid sequences or two nucleotide sequences are considered "homologous" if they have an alignment score of >5 (in standard deviation units) using the program ALIGN with the mutation gap matrix and a gap penalty of 6 or greater (Dayhoff, M. O., in Atlas of Protein Sequence and Structure (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, 70%, 80%, 90%, 95%, or even 98% identical when optimally aligned using the ALIGN program mentioned above.

"Modulate" intends a lessening, an increase, or some other measurable change, e.g., in the stability or biological function of a protein.

A "small molecule ligand" is a discrete small-molecule, well known in the pharmaceutical and material sciences, which is to be distinguished from, e.g., a polypeptide or nucleic acids, which is a polymer consisting of monomeric subunits. Small molecule ligands may be naturally-occurring or synthetic as exemplified by pharmaceutical products, laboratory reagents, and the like.

As used herein, a "variant" protein is a protein having an amino acid sequence that does not occur in nature, as exemplified by sequences in GenBank.

As used herein, a "mutant" is a mutated protein designed or engineered to alter properties or functions relating to protein stabilization and/or ligand binding.

2. Overview

The present composition, system, and method (generally, "system") relate to the conditional stabilization of a protein of interest (POI) fused to a single-polypeptide chain, ligand-dependent, stability-affecting protein. The stability-affecting protein, also referred to as a ligand-binding domain, can be preselected to confer either stability or instability to the entire fusion protein, depending on the presence or absence of the ligand.

A feature of the conditional protein stability system is that the stability-affecting protein is of a "single ligand-single domain" type, which minimizes the number of components in the system. The system is illustrated using two different ligand-binding domains, namely, the FK506-binding protein (FKBP) and dihydrofolate reductase (DHFR), binding domains, in combination with appropriate ligands, Experiments performed in support of the systems are described below, along with embodiments and examples of the system.

3. Stability-Affecting Protein Derived from FKBP a. Introduction

Rapamycin and FK506 are commercially available, cell-membrane permeable, FDA-approved immunosuppressive agents, which are ligands of the FK506-binding protein (FKBP12 or FKBP). The FKBP-rapamycin complex binds to the FKBP-rapamycin-binding (FRB) domain of the FKBP-rapamycin-associated protein (FRAP). FRAP is also known as the mammalian target of rapamycin (mTOR), rapamycin and FKBP target 1 (RAFT1), and sometimes FRB. Rapamycin complexed with FKBP binds to and inhibits FRAP/mTOR at its FRB domain, which eventually inhibits/delays cell cycle progression through $G_1$ (see, e.g., Choi, J. et al. (1996) Science 273:239-42 and Vilella-Bach, M. et al, (1999) J. Biol. Chem. 274:4266-72). Fusion polypeptides may be made between a protein of interest (PO) and either FKBP and/or the FRB domain of FRAP/mTOR. Colocalization of the protein(s) of interest is induced upon addition of rapamycin.

Because rapamycin has inherent biological activity, researchers developed a "bump-hole" strategy (similar to that employed by Shokat and coworkers), wherein rapamycin derivatives with bulky side-chain substituents would bind poorly to the FRB domain of a wild-type/naturally-occurring FRAP/mTOR. Binding was restored by introducing compensatory hole/cavity-forming mutations in the FRB domain. In particular, the bulky side chain of a C20-methallyl-rapamycin derivative (MaRap) is accommodated by a triple-substituted variant of FRB called FRB* (Liberles et al., 1997).

In fusing the FRB and FRB* domains to a kinase (GSK-3β) it was discovered that the levels of the GSK-3β-FRB* fusion protein were substantially decreased compared to an otherwise identical GSK-3β-FRB fusion protein. The levels of the FRB* fusion protein were rescued (i.e., increased to levels similar to those of the FRB fusion protein) upon the addition of MaRap. FRB* appeared to confer conditional instability to multiple different proteins in the absence of MaRap, with stabilization being dependent on the interaction of two proteins (i.e., FKBP and FRB) via a small molecule (MaRap) that is expensive, difficult to synthesize and formulate, and exhibits poor pharmacokinetic properties in vivo.

b. Drug-ON System

The 107-residue FK506 and rapamycin-binding protein (FKBP) was selected for use as a destabilizing domain in a "drug-ON" system. FKBP has been widely studied, often in the context of fusion proteins, and numerous high-affinity ligands for FKBP have been developed (Pollock and Clackson, 2002). In one study, ligands that possess a synthetic "bump" in the FKBP-binding domain were shown to bind more tightly to a mutated FKBP having a cavity formed by the removal of an aromatic side chain (i.e., harboring the substitution, F36V). Such engineered ligands bind preferentially to the mutated FKBP12 compared to the wild-type/naturally-occurring protein by almost three orders of magnitude (Clackson et al., 1998). Moreover, this family of ligands does not elicit undesired responses when administered to cultured cells or animals, including humans (Iuliucci et al., 2001).

FIG. 1A illustrates a method for conditionally controlling protein stability using a fusion protein containing a destabilizing domain (DD) derived from FKBP fused in-frame to a protein of interest (POI). In the absence of a stabilizing ligand, the destabilizing domain mediates the degradation of the entire fusion protein. The addition of an appropriate ligand stabilizes the destabilizing domain, greatly reducing degradation of the fusion protein. Using such FKBP polypeptides and ligands, a single unstable ligand-binding domain is able to direct the degradation of a POI, avoiding the need to assemble the FKBP-rapamycin-FRAP/mTOR ternary complex to regulate protein function.

To identify FKBP variants (i.e., mutants) with a high affinity for the synthetic FKBP ligand, SLF* (FIG. 1B) a cell-based screening assay was used to screen a library based on the FKBP F36V gene sequence, which was cloned in-frame with yellow fluorescent protein (YFP) as a reporter protein/protein of interest. In this manner, YFP fluorescence served as an indicator of FKBP stability. The FKBP-YFP fusion protein library (i.e., a library of N-terminal FKBP mutants) was introduced into NIH3T3 fibroblasts using a retroviral expression system. The transfected/transduced cells were subjected to three rounds of sorting using flow cytometry, as illustrated in FIG. 1C. The cells were treated with SLF* (FIG. 1B) in the first round of sorting. The fluorescent cells were collected, cultured in the absence of ligand (second round), and then cultured again in the presence of SLF* (third round), at which time YFP-expressing cells were collected and the genomic DNA was isolated for sequence analysis (Example 7). All sequences analyzed maintained the F36V mutation (not reflected in the nomenclature), along with other frequently recurring amino acid mutations (Table 1).

Five variants (F15S, V24A, H25R, E60G, and L106P) were selected for further analysis. These variant FKBP-derived, ligand-responsive destabilizing domains were separately transduced into NIH3T3 cells and assayed for stability in the presence and absence of a ligand called Shield1, which was a derivative of SLF* in which the carboxylic acid was replaced with a morpholine group at a position unlikely to interfere with FKBP binding (Example 8, FIG. 1B).

Figure 2:
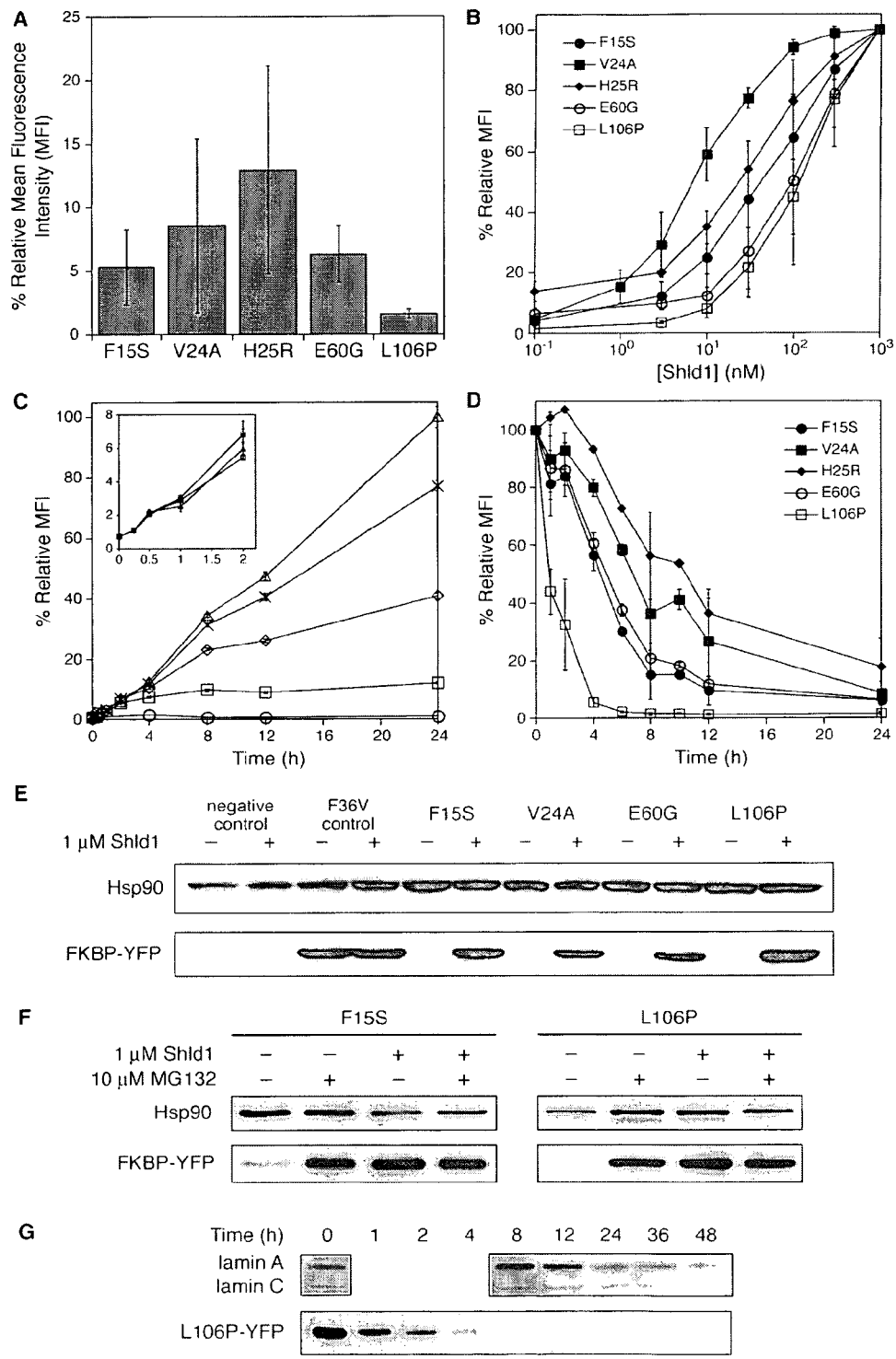
FIGS. 2A-2D are graphs showing the results of experiments to characterize FKBP variants that display Shield1-dependent stability. The data for FIGS. 2A-2D are presented as the average mean fluorescence intensity (MFI)±SEM relative to that of the maximum fluorescence intensity observed for the individual mutant. Experiments were performed in triplicate.
FIGS. 2E-2G show the results of immunoblot analysis to characterize FKBP variants that display Shield1-dependent stability.

All five variants showed decreased levels of fluorescence with respect to a positive control, indicating that the variants obtained from the library screen were destabilizing (FIG. 2A). The most destabilizing variation, L106P, produced YFP fluorescence at a level of only 1-2% relative to the positive control. All FKBP-derived, ligand-responsive destabilizing domain variants produced increased fluorescence signal when incubated in the presence of Shield1 (FIG. 2B). Variant V24A showed the most efficient rescue (i.e., stabilization by Shield1) with an $EC_{50}$ of about 5 nM. Variant L106P required a higher concentrations of Shield1 to stabilize the YFP fusion protein ($EC_{50}$~100 nM). YFP fluorescence increased at approximately the same rate in all the transfected cells upon addition of Shield1, with maximum fluorescence being achieved at 24 hours and stably maintained for at least an additional 48 hours without further addition of Shield1 (FIG. 2C).

Figure 12:
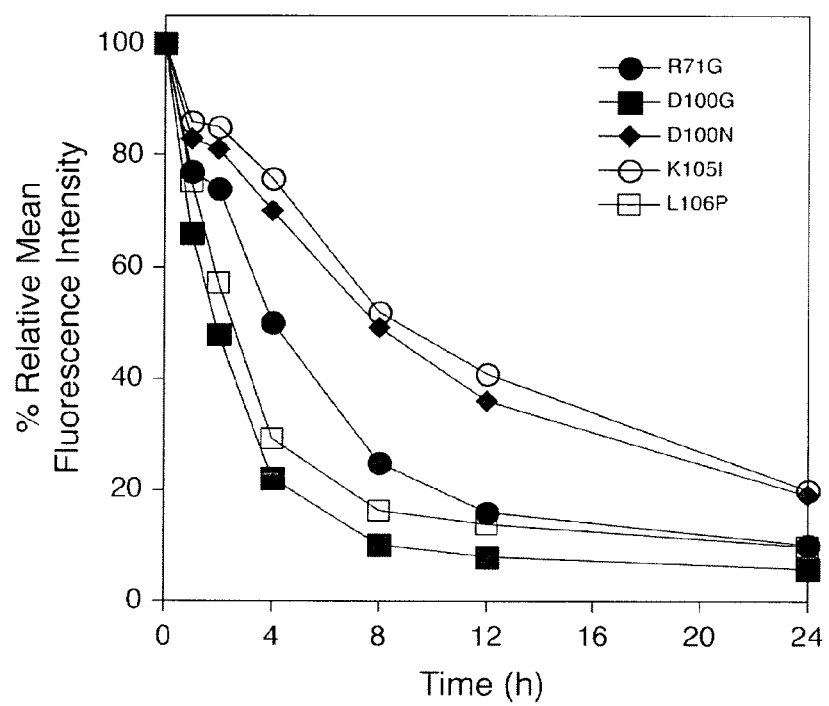
FIG. 12 is a graph showing the kinetics of decay of YFP-FKBP fluorescence upon removal of Shield1. NIH3T3 cells stably expressing YFP-FKBP fusion proteins were treated with 1 μM Shield1 for 24 hours, at which point the cells were washed with media to remove Shield1. The decrease in fluorescence was monitored using flow cytometry. Data are presented as the average mean fluorescence intensity relative to that of the maximum fluorescence intensity observed for the individual mutant.

Upon withdrawal of Shield1, distinct differences in fluorescence decay profiles were observed among the FKBP-derived, destabilizing domain variants (FIG. 2D), revealing a correlation between the rate of degradation and the degree of destabilization. Variant H25R, which is the least destabilizing of this group, showed the slowest rate of degradation, whereas L106P, the most destabilizing of the five, was degraded most quickly, with protein levels becoming negligible within four hours. Similar results were obtained upon withdrawal of Shield1 from C-terminal variant FKBP fusions, as shown in FIG. 12.

Figure 9:
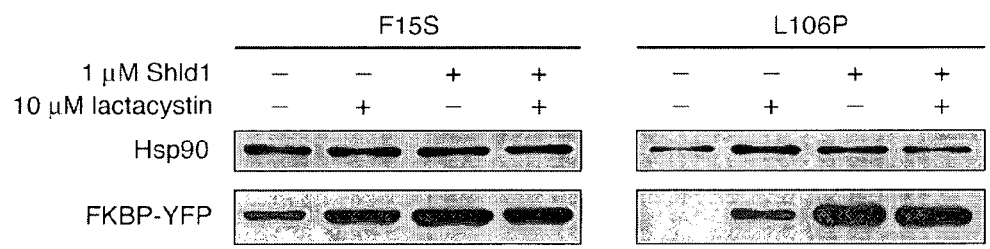
FIG. 9 shows the results of immunoblot analysis demonstrating that degradation of FKBP-YFP fusions is mediated by the proteosome. NIH3T3 cells stably expressing F15S-YFP and L106P-YFP were treated with 1 μM Shield1 for 24 hrs. The cells were then washed and treated with 10 μM lactacystin in the presence and absence of 1 μM Shield1 for 4 hrs. Immunoblot analysis was performed using an anti-YFP antibody.

These results were confirmed by immunoblot analysis using antibodies specific for either FKBP (FIG. 2E) or YFP (data not shown), which were incapable of detection in protein lysates from mock-treated cells, but detectable in detected in protein lysates from Shield1-treated cells (Example 8). Incubation of the transfected cells with MG132 (FIG. 2F) or lactacystin (FIG. 9), which are drugs that inhibit ubiquitin-proteasome-mediated protein degradation, inhibited degradation of the variant FKBP fusion proteins following the withdrawal of Shield1, indicating that degradation was mediated, at least in part, by the proteasome.

Figure 3:
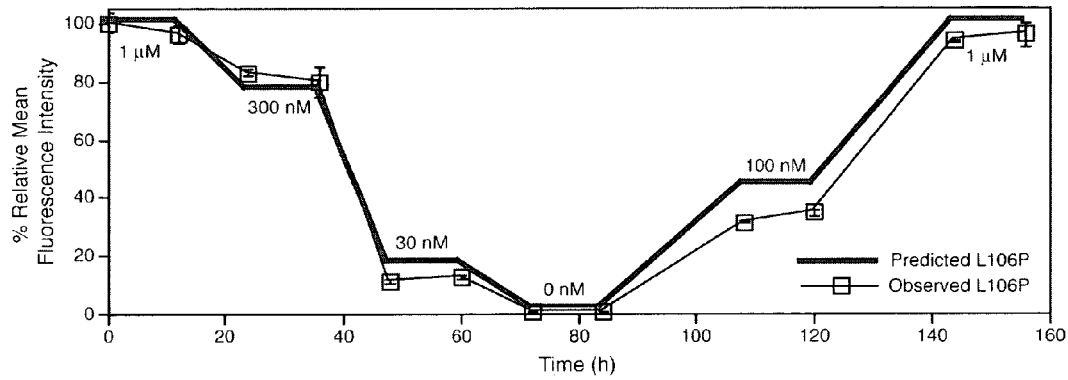
FIG. 3 is a graph showing the reversible nature of small-molecule regulation of intracellular protein levels. A population of NIH3T3 cells stably expressing the L106P-YFP fusion protein was treated with different concentrations of Shield1 over the course of one week, and samples of the population were assayed for fluorescence by flow cytometry at the indicated time points. Predicted fluorescence is based on the dose-response experiment shown in FIG. 2B.
Figure 8:
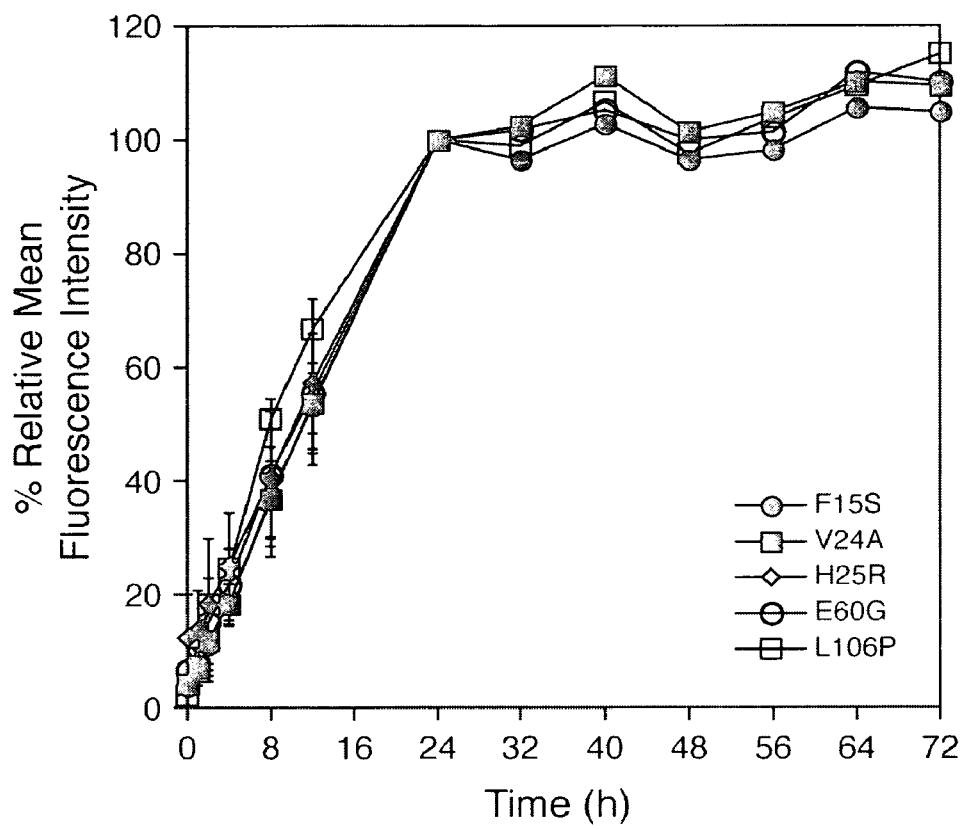
FIG. 8 is a graph showing the kinetics of FKBP-YFP fluorescence in cells upon addition of Shield1. NIH3T3 cells stably expressing the indicated FKBP-YFP fusions were treated with 1 μM Shield1, and increases in fluorescence were monitored over time using flow cytometry. Data are presented as the average mean fluorescence intensity (MFI)±SEM relative to that of the maximum fluorescence intensity observed for the individual variant. The experiment was performed in triplicate, and MFI was normalized to 100% at 24 hr.

FIG. 3 shows the results of an experiment demonstrating the reversible nature of small-molecule regulation of intracellular protein levels. A population of NIH3T3 cells stably expressing the L106P-YFP fusion protein was treated with different concentrations of Shield1 over the course of one week, and samples of the population were assayed for fluorescence by flow cytometry at the indicated time points. Predicted fluorescence is based on the dose-response experiment shown in FIG. 2B. FIG. 8 shows the kinetics of fluorescence in cells stably expressing one of several FKBP-YFP fusion proteins upon addition of Shield1.

Figure 10:
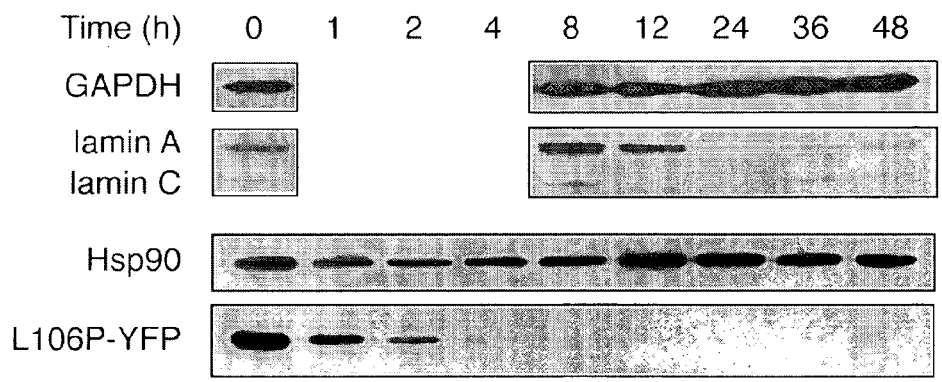
FIG. 10 shows the results of immunoblot analysis comparing the kinetics of destruction-domain-mediated degradation to the kinetics of RNAi-mediated silencing. HeLa cells were transfected with 30 nM siRNA against lamin A/C and monitored over time. The time required for the reduction in levels of lamin A/C was compared to the time required for the degradation of L106P-YFP upon removal of Shield1 from the cells stably expressing the fusion protein.

To compare the present methods with those known in art for regulating gene expression, the rate of degradation of a protein of interest achieved using the FKBP-derived, destabilizing domain variants, was compared to RNAi-mediated silencing of another endogenous gene, Lamin A/C, a non-essential cytoskeletal protein commonly used as a control in RNAi experiments. Previous studies have shown more than 90% reduction in lamin A/C expression in HeLa cells 40 to 45 hours following transfection of the cells with a cognate siRNA duplex (Elbashir et al., 2001). In line with published results, HeLa cells transfected with siRNA against lamin A/C showed a decrease in lamin A/C levels after 24 hours, with a significant reduction in lamin A/C observed by 48 hours (FIGS. 2G and 10). In contrast, cells stably expressing L106P-YFP show nearly complete degradation of the fusion within 4 hours of removal of Shield1. These results demonstrate that fusion of a destabilizing domain to a protein of interest dramatically reduces its stability in cultured cells, causing the protein of interest to be quickly degraded upon removal of the stabilizing ligand (Example 8).

Further experiments demonstrated that, NIH3T3 cells stably expressing the L106P-YFP variant produced YFP fluorescence in a dosage-dependent manner with respect to the amount of ligand present (Example 9). The results obtained using N-terminal destabilizing domains are shown in FIG. 2B. C-terminal destabilizing domains responded to Shield1 in a dose-dependent manner comparable to N-terminal destabilizing domains, with $EC_{50}$ values ranging from 10 nM to 100 nM (Example 10, FIG. 11, and Table 2). Ligand-dependent protein stability was also observed in NIH3T3, HEK 293T, HeLa, and COS-1 cells that were transfected with the FKBP-derived fusion proteins (Example 11, Table 3), demonstrating that ligand-dependent stability is not restricted to one cell type.

Figure 4:
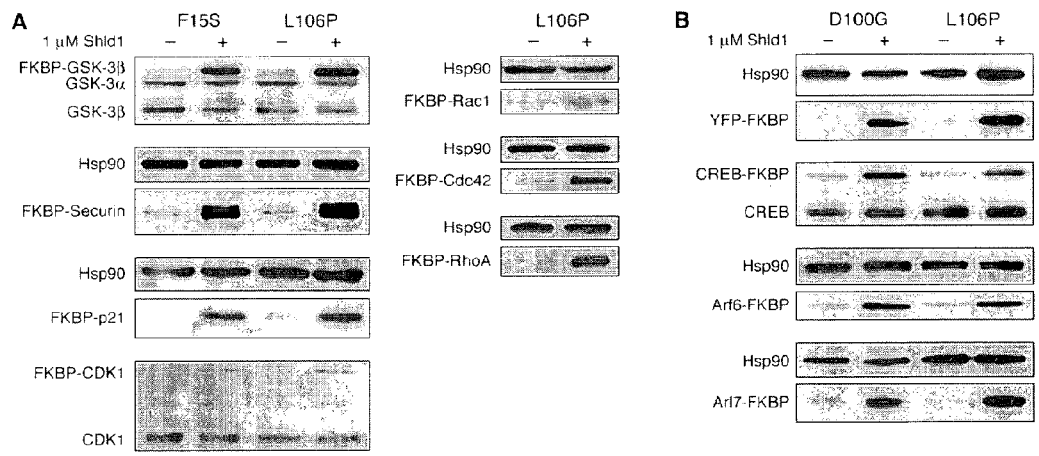
FIGS. 4A and 4B show the results of immunoblot analysis demonstrating that the FKBP destabilizing domain confers Shield1-dependent stability to a variety of different proteins.

FKBP variants were efficient in destabilizing proteins other than YFP, e.g., the kinases GSK-3β and CDK1, the cell cycle regulatory proteins securin and p21, and three small GTPases, Rac1, RhoA and Cdc42 (FIG. 4A). All these N-terminal fusion proteins demonstrated Shield1-dependent stability, with the absence of Shield1 resulting in the degradation in a Shield1-dependent manner (Example 12).

Figure 5:
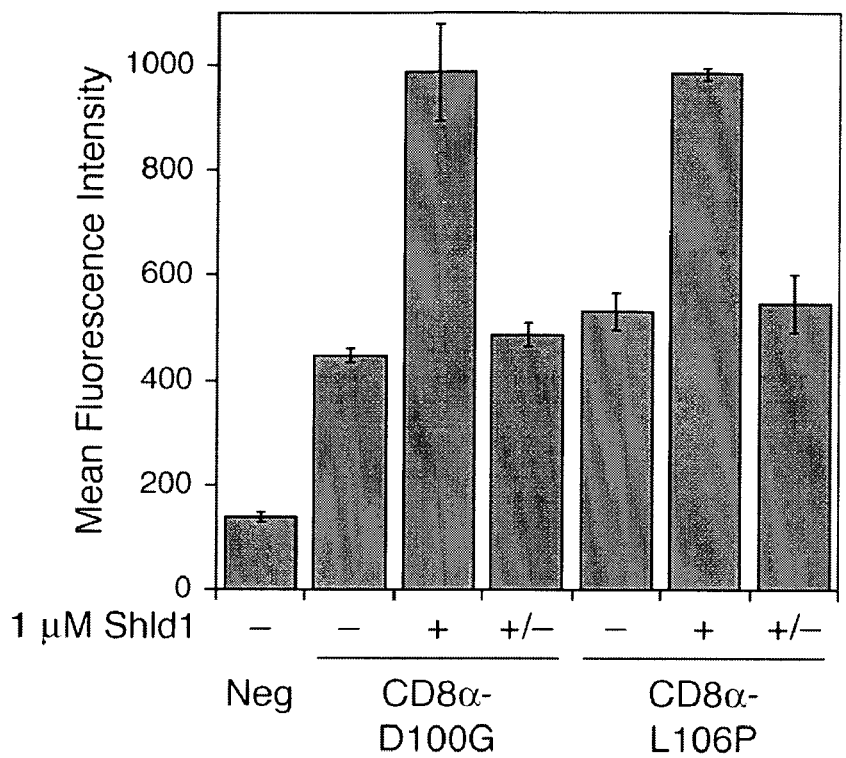
FIG. 5 is a graph showing that the destabilizing domain confers Shield1-dependent stability to a transmembrane protein. FKBP variants D100G and L106P were fused to the C-terminus of CD8α. NIH3T3 cells stably expressing the fusion proteins were divided into three pools (groups). The first group (−) was mock-treated, the second group (+) was treated with 1 μM Shield1 for 24 hrs, and the third group (+/−) was treated with 1 μM Shield1 for 24 hrs, and then washed with media and cultured for 24 hr in the absence of Shield1. Live cells were then probed with a FITC-conjugated anti-CD8α antibody and assayed by flow cytometry. Data are presented as the average mean fluorescence intensity±SEM from an experiment performed in triplicate.

FKBP variants were also efficient in destabilizing proteins other than YFP, e.g., the transcription factor CREB, or the small GTPases Arf6 or Arf7, when the FKBP mutant is fused at the C-terminus of the protein of interest (FIG. 4A). All these C-terminal fusion proteins demonstrated Shield1-dependent stability, with the absence of Shield1 resulting in the degradation in a Shield1-dependent manner (Example 12). As shown in FIG. 5, the destabilizing FKBP variants D100G (SEQ ID NO: 7) and L106P (SEQ ID NO: 6) also conferred Shield1-dependent stability to a transmembrane protein, CD8α, when fused at the C-terminus of the transmembrane protein.

Moreover, cell morphology could be manipulated by the presence or absence of Shield1 (Example 13). Shield1-treated cells displayed the predicted morphologies, i.e., expression of RhoA induced the formation of stress fibers, expression of Cdc42 resulted in filopodia formation, and expression of Arl7 induced the shrunken cell phenotype (Heo and Meyer, 2003), while mock-treatment with Shield1 produced cells with fibroblast-like morphologies. These GTPase-dependent morphology changes were reversible, as treatment with Shield1 followed by removal of Shield1 also produced cells with fibroblast-like morphologies. The penetrance of the observed phenotype was high, with a large percentage of cells (>90%) exposed to a given experimental condition displaying the predicted behavior (data not shown).

Figure 13:
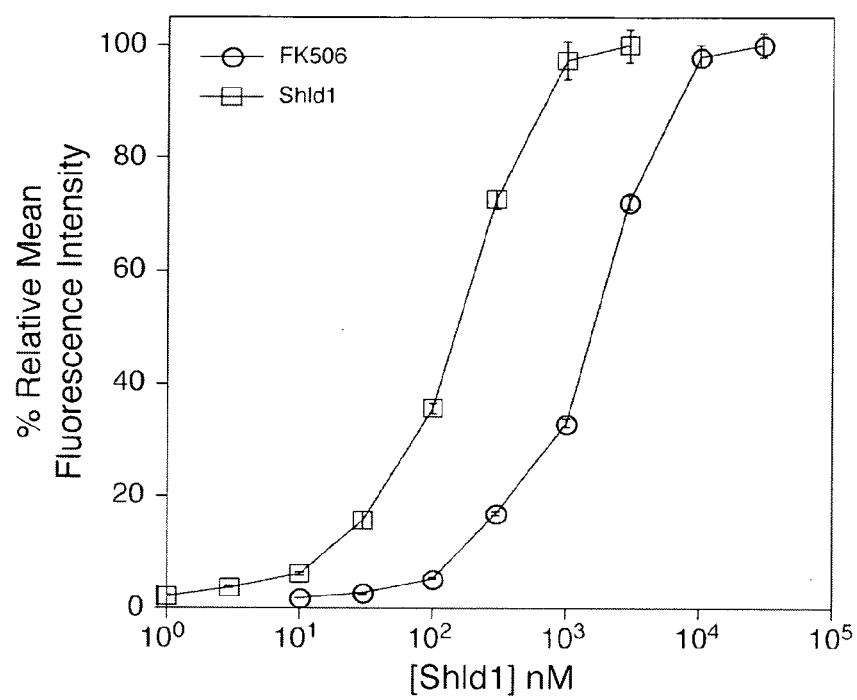
FIG. 13 is a graph showing that FKBP-YFP fusion proteins are stabilized by multiple FKBP ligands. NIH3T3 cells stably expressing the L106P-YFP fusion were treated with three-fold dilutions of FK506 (30 μM to 10 nM) or Shield1 (3 μM to 0.1 nM) and fluorescence was monitored by flow cytometry. Data are presented as the average mean fluorescence intensity±SEM relative to that of the maximum fluorescence intensity observed for the L106P-YFP mutant. Experiments were performed in triplicate.

The FKBP-derived destabilizing domains can be stabilized using Shield1 as well as the commercially available ligand, FK506 (FIG. 13).

b. Drug-OFF System

The above-described FKBP-derived conditional protein stability system uses a variant of FKBP to stabilize a POI in the presence of an appropriate ligand, and destabilize the POI in the absence of the ligand, representing a "drug-ON" system. In a related embodiment of the system, a variant FKBP polypeptide sequence was used to destabilize a POI in the presence of an appropriate ligand, and stabilize the POI in the absence of the ligand, representing a "drug-OFF" system.

Figure 6A:
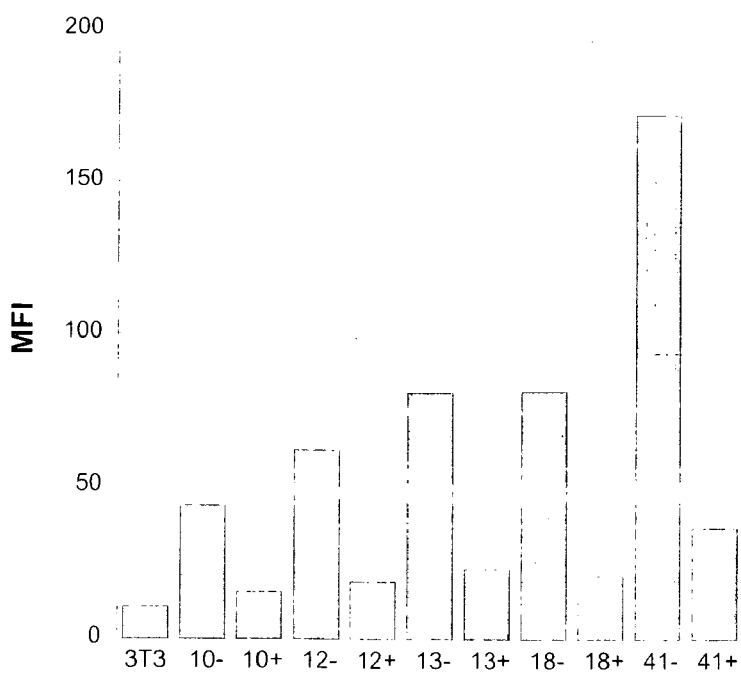
FIG. 6A shows the results of an experiment using a "drug-OFF" system, in which a FKBP protein attached to a diversity element sequence was fused to YFP. YFP fluorescence could be detected by FACS analysis in the absence of the ligand (Shield1) but was almost undetectable in the presence of the ligand (n=5 clones).

Variant FKBP polypeptide sequences having the desired properties were identified by preparing a library of sequences encoding FKBP (F36V) with a short, 20-amino acid diversity element (i.e., population of sequences encoding different amino acids) fused at the C-terminus of FKBP. The FKBP-diversity element sequences were fused to the C-terminus of YFP, as before, and the sequences encoding the YFP-FKBP-diversity element were introduced into NIH3T3 cells for screening. Five different clones were identified in which YFP could be detected by FACS analysis in the absence of the ligand (Shield1) but was nearly undetectable in the presence of the ligand (i.e., a 5 to 6-fold decrease in the presence of ligand; FIG. 6A). The sequence encoding the FKBP-diversity element variants were recovered from the cells and sequenced, revealing that all five clones encoded the same diversity element sequence, namely TRGVEEVAEGVVLL-RRRGN (SEQ ID NO. 18). Thus, a FKBP polypeptide fused to the selected diversity element functioned as a stabilizing domain in the absence of ligand, rather than a destabilizing domain, as is characteristic of, e.g., the F36V/L106P FKBP mutant and other mutants.

The "drug-OFF" system offers some advantages over the "drug-ON" system. In particular, the "drug-OFF" system requires the presence of the ligand only to destabilize the POI. Thus, where the POI is essential for viability, the absence of the ligand allows the protein to function normally. In contrast, in a "drug-ON" system, the ligand must be present at all times, except where the effect of removing the POI is being studied. Since the cost of maintaining cells or animals in the presence of ligand over a prolonged period of time can be considerable, the "drug-OFF" system can be more economical.

c. Use of the System in Other Eukaryotic Organisms

While the FKBP system was first characterized in mammalian cells, further experiments have demonstrated that the system works in eukaryote parasites, particularly *Toxoplasma* and *Plasmodium*.

Figure 6B:
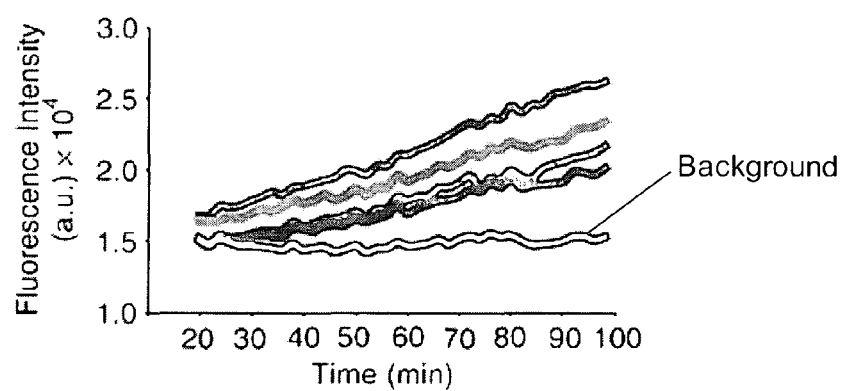
FIGS. 6B and 6C shows the results of an experiment performed in *Toxoplasma*. The fluorescence of parasitophorous vacuoles in infected cells was monitored by time lapse microscopy following addition (FIG. 6B) or removal of ligand (FIG. 6C). Background fluorescence is indicated.
Figure 6C:
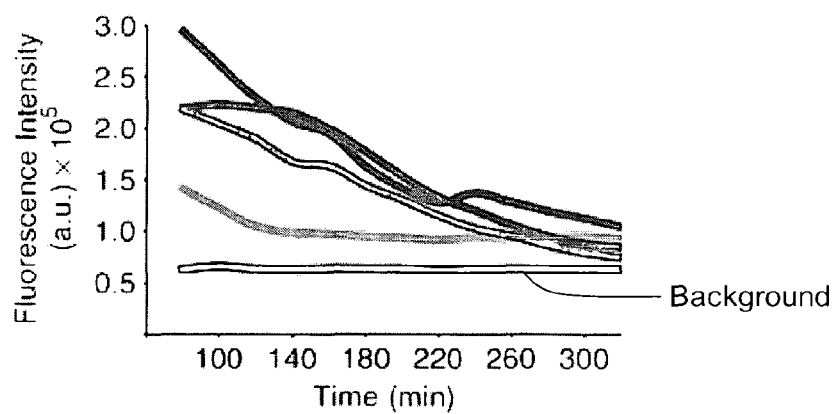

FIGS. 6B and 6C shows the results of experiments performed in a *Toxoplasma gondii* system, in which an FKBP-derived stability-affecting domain was fused to the N-terminus of YFP. Nucleotides expressing the fusion the fusion protein were introduced into *T. gondii* parasites, which were then used to infect HFF cells. The parasitophorous vacuoles in the infected cells were monitored by time lapse fluorescence microscopy following the addition of ligand (Shield1; FIG. 6B) or following the removal of ligand (FIG. 6C). The indicated control line corresponds to background fluorescence, while each of the other lines in the graphs correspond to individual infected cells. The results show that the levels of YFP increase in the presence of ligand and decrease in the absence of ligand, demonstrating that the conditional protein stability system is effective in *Toxoplasma*.

Figure 6D:
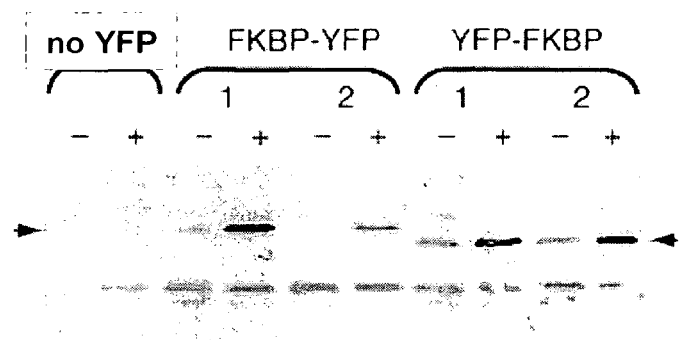
FIGS. 6D and 6E shows the results of an experiment performed in a *Plasmodium*. An antibody to YFP protein was used to detect fusion proteins in transfected cells, which are greatly increased in the presence of ligand.
Figure 6E:
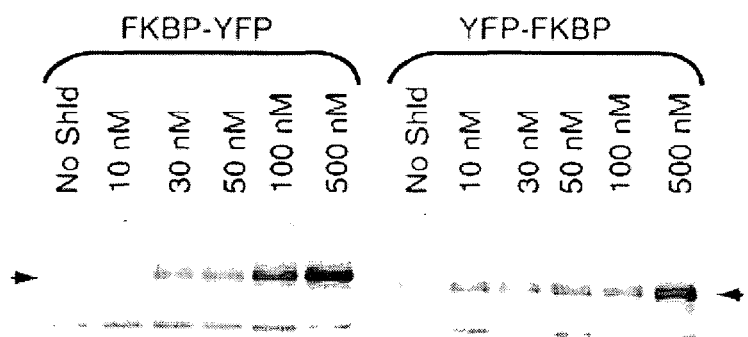

In another illustration of use of the system in eukaryotic parasites, FIGS. 6D and 6E shows the results of an experiment performed in a *Plasmodium falciparum*. The immunoblot shows the levels of YFP fusion protein in transfected cells, which are greatly increased in the presence of ligand. In a related experiment, fusion proteins were made with falcipain-2, a cysteine protease. Knocking out the falcipain-2 gene causes vacuole swelling resulting from the decreased ability of the organisms to degrade hemoglobin. Fusion of falcipain-2 to the F36V/L106P FKBP mutant produced a conditional falcipain stabilization system. More than 5-times as many organisms demonstrated the swollen vacuole phenotype in the presence of ligand (Shield1), compared to the absence of ligand.

d. Use of the System In Vivo

HCT116 cancer cells were transfected with a nucleic acids encoding the reporter gene luciferase fused to an FKBP-derived stability-affecting protein (F36V/L106P) mutant. Stable transformants were then selected and used to challenge SCID mice.

Figure 7:
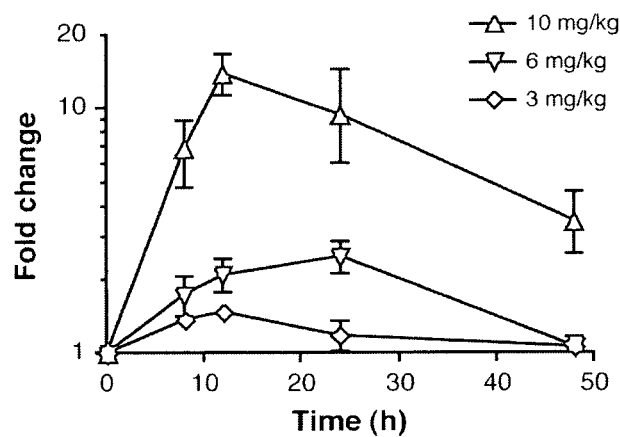
FIGS. 7A and 7B are graphs showing the results of an experiments in which SCID mice were challenged with tumor cells genetically manipulated to express luciferase fused to a stability-affecting protein.
Figure 7:
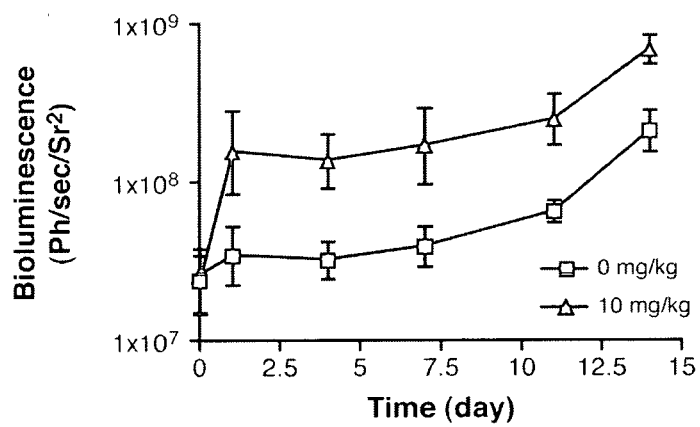

The results of an experiments in which SCID were challenged with tumor cells harboring nucleic acids encoding luciferase fused to an FKBP-derived, stability-affecting protein (F36V/L106P) are shown in FIGS. 7A and 7B. The mice were either untreated or treated with the indicated amounts of ligand (Shield1) and bioluminescent signals were imaged over time as described (Lin, A. H., et al. (2005) *J. Immunol.*

175:547-54; Luo, J., et al. (2006) *Proc. Nat'l. Acad. Sci. USA* 103:18326-31; n=4-10 mice per treatment group).

The graph in FIG. 7A shows that the amount of luminescence is dependent on ligand dose, and that luminescence peaks at about 10 hours following a single injection of ligand. The graph shown in FIG. 7B shows that repeated administration of the ligand (10 mg/kg Shield1 every 48 hours) results in continued luciferase stabilization. These results demonstrate that the conditional protein stabilization systems work in vivo, where the ligand is delivered to cells via the blood stream of an animal.

4. Stability-Affecting Protein Derived from DHFR

Dihydrofolate reductase (DHFR) is a ubiquitous enzyme involved in the regeneration of tetrahydrofolate from dihydrofolate, using NADPH. The goal was to use *E. coli* DHFR as a destabilizing domain (DD) when fused at either the N or the C-terminus of a protein of interest (POI). Since DHFR is an enzyme present in mammalian cells, mutants of DHFR having reduced catalytic ability were used to minimize perturbations to the intracellular environment caused by the introduction of an exogenous DHFR. Two of these mutations, Y100I (SEQ ID NO: 14) and G121V (SEQ ID NO: 15), in addition to reducing enzymatic activity, also destabilized DHFR relative to the wild-type sequence (SEQ ID NO: 13).

Figure 14:
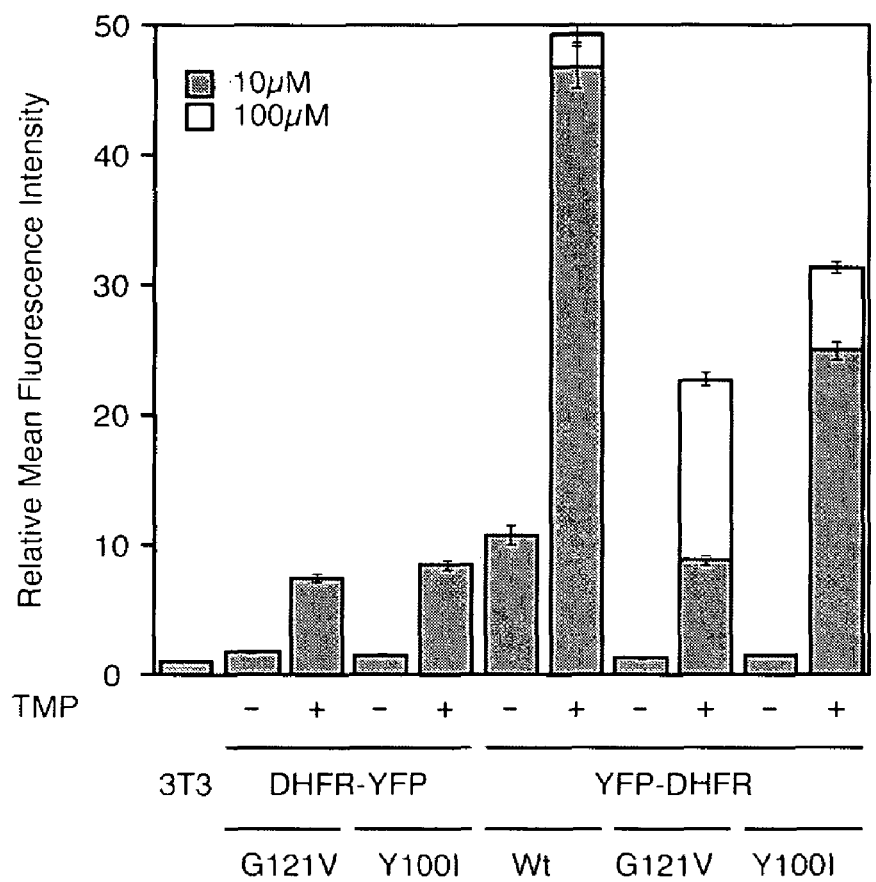
FIG. 14 is a graph showing fluorescence levels obtained using YFP-DHFR and YFP-DHFR fusion proteins. YFP fused to wild-type, G121V, and Y100I versions of DHFR were subjected to fluorescence analyses in the presence of 10 μM or 100 μM TMP.
Figure 15:
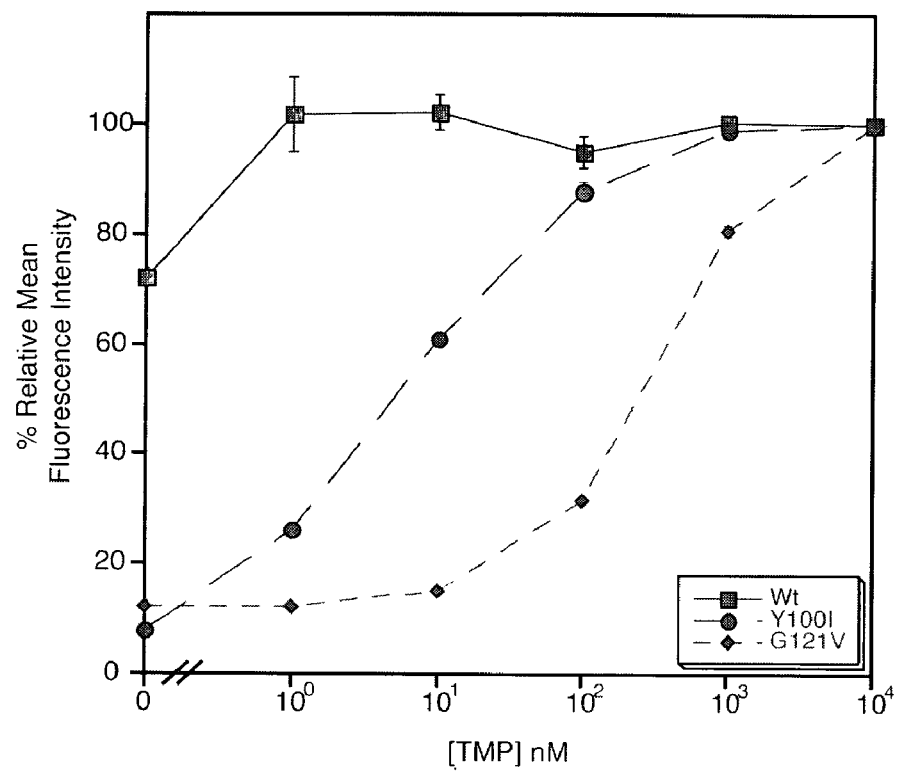
FIG. 15 is a graph showing fluorescence levels in NIH3T3 cells stably expressing DHFR-YFP fusion proteins and treated with ten-fold dilutions of TMP (10 μM to 1 nM), or mock-treated with DMSO. The fluorescence levels were monitored by flow cytometry. MFI was normalized to 100% of cells treated with 10 μM TMP at 24 hrs.

These DHFR mutants acted as destabilizing domains when fused to yellow fluorescent protein (YFP) at either the N- or the C-terminus of the YFP reporter (FIG. 14). While fusion of the mutated DHFR to either the N or C-terminus of the YFP reporter resulted in ligand-dependent stabilization of the YFP reporter in the presence of trimethoprim (TMP; indicated by "+") compared to the absence of TMP (indicated by "−"), the effect was most pronounced when the Y100I and G121V DHFR were fused to the N-terminus of the YFP reporter (FIG. 15).

To further improve the ligand-dependent stabilization characteristics of the DHFR-derived destabilizing domains for use at the C-termini of POIs, error-prone PCR was used to generate a library of additional mutants of DHFR, similar to manner in which mutants of FKBP were generated. The YFP-DHFR fusion protein library (i.e., the library of C-terminal DHFR mutants) was introduced into NIH3T3 fibroblasts using a retroviral expression system, as before, and the transduced cells were subjected to four rounds of sorting using flow cytometry. The cells were cultured in the absence of ligand in the first round of sorting. Low YFP-expressing cells were collected, cultured in the presence of 10 µM TMP for 24 hours (i.e., the second round of sorting), and then again cultured in the presence of 1 µM TMP (i.e., the third round of sorting) to isolate YFP-expressing cells with increased ligand-dependent stabilization.

Cells that displayed fluorescence were cultured in the presence of TMP, washed free of TMP, and sorted about four hours later to isolate mutants with fast kinetics of degradation in the fourth round of sorting. Low YFP-expressing cells (i.e., cell in which YFP was most degraded following the removal of the TMP from the cell medium), were collected, and the genomic DNA was isolated for sequence analysis. In this manner, two additional DHFR-derived destabilizing domains, having increased ligand-dependent stabilization, were isolated from the library screen, i.e., one double-mutant (N18T/A19V; SEQ ID NO: 17) and one single-mutant (F103L; SEQ ID NO: 16).

Figure 16:
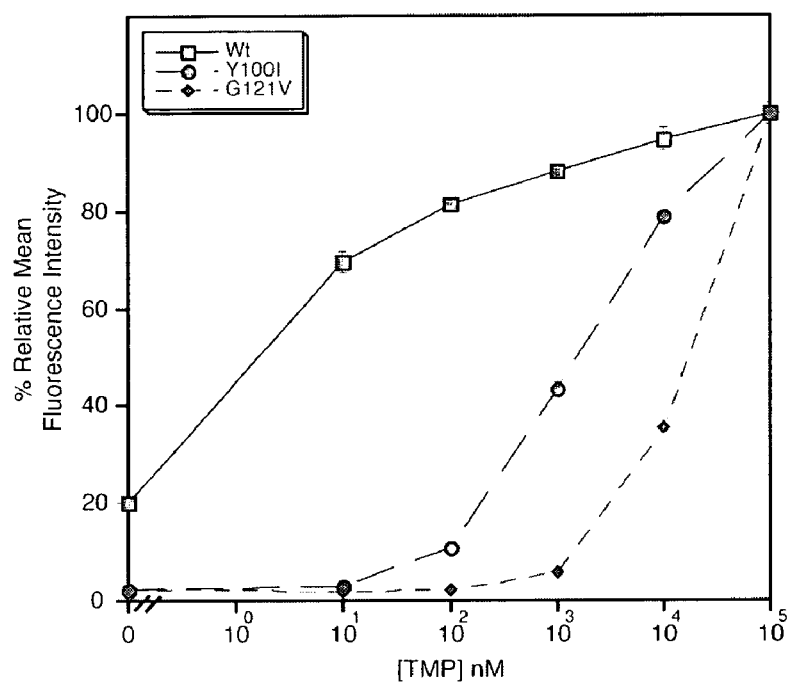
FIGS. 16A and 16B are graphs showing YFP fluorescence levels in NIH3T3 cells expressing YFP-DHFR fusion proteins and treated with ten-fold dilutions of TMP, or mock-treated with DMSO.
Figure 16:
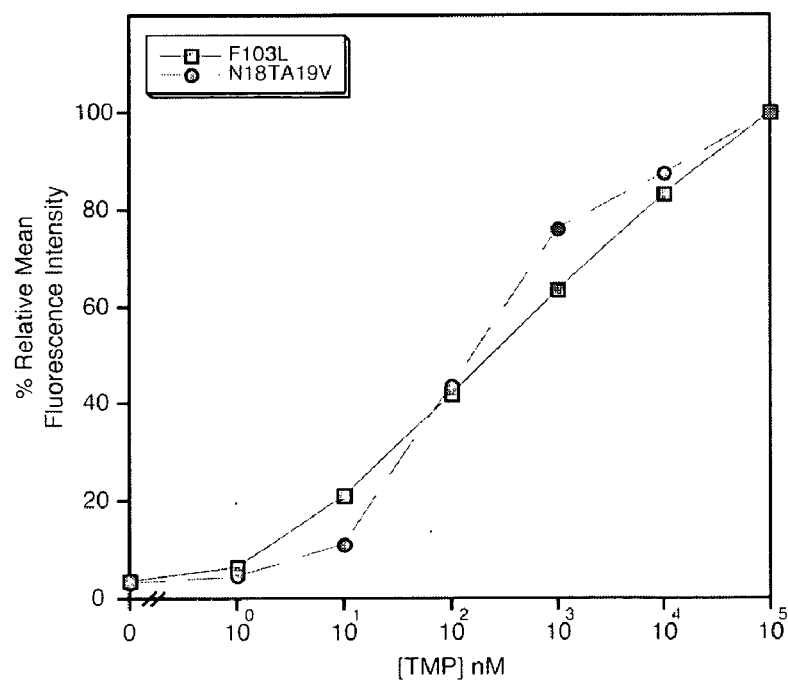
Figure 17:
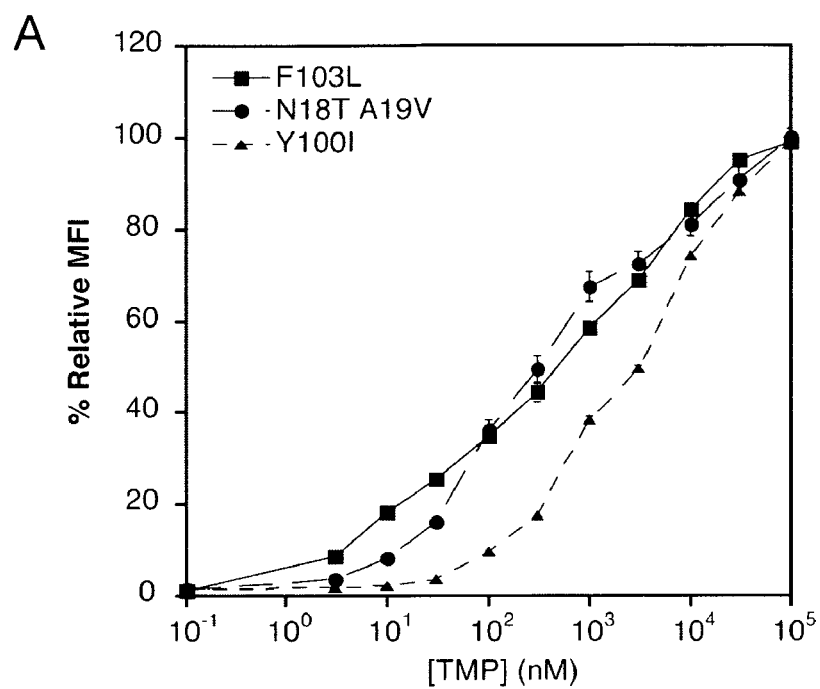
FIG. 17A is a graph showing a comparison of the stability of YFP fused at the N-terminus of several DHFR mutants.
FIG. 17B shows the results of an immunoblot experiment using an antibody specific for YFP in the presence and absence of ligand.
Figure 17:
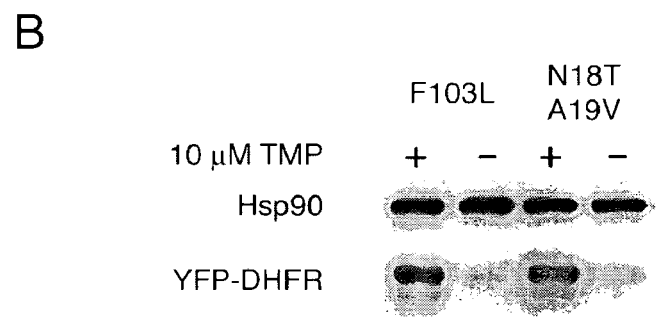

When fused to the C-terminus of YFP, these mutants destabilized YFP in the absence of TMP and stabilized YFP in the presence of TMP. As shown in FIGS. 16A and 16B, the N18T/A19V and F103L DHFR mutants were effectively stabilized by lower concentrations of TMP relative to the original Y100I and G121V mutants. A comparison of the F103L, N18T/A19V, and Y100I DHFR mutants fused to the C-terminus of YFP is shown in FIG. 17A. An immunoblot performed using an antibody specific for DHFR confirmed that the amount of DHFR present in cells is increased in the presence of ligand (+) compared to the absence of ligand (−) (FIG. 17B).

Figure 18:
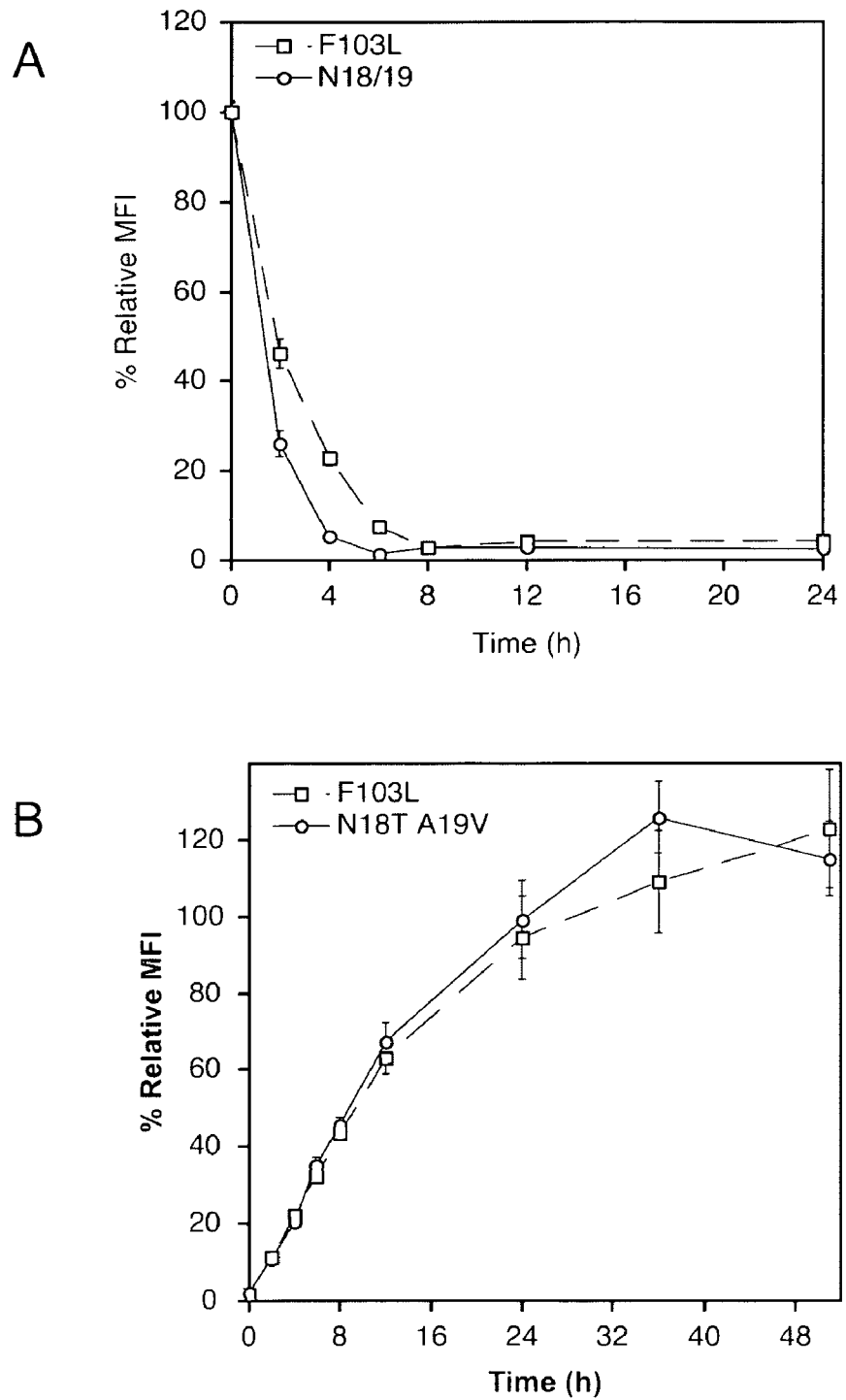
FIG. 18A is a graph showing the kinetics of YFP-DHFR decay following withdrawal of ligand.
FIG. 18B is a graph showing the kinetics of YFP-DHFR stabilization following addition of ligand.

The kinetics of YFP-fusion protein decay following withdrawal of ligand is shown in FIG. 18A. The rate of decay of the C-terminal fusion protein harboring the F103L DHFR mutant was more rapid that of the C-terminal fusion protein harboring the N18T/A19V DHFR mutant, although the levels of both proteins were similar by eight hours following withdrawal of the ligand. The kinetics of YFP-fusion protein stabilization following the addition of ligand is shown in FIG. 18B. The amount of YFP detectable in cells initially increased linearly following addition of ligand, eventually reaching a maximum level.

To further improve the ligand-dependent stabilization characteristics of the DHFR-derived, stability-affecting proteins for use at the N-termini of POIs, error-prone PCR was used to generate a library of additional mutants of DHFR, similar to manner in which mutants of FKBP were generated. Using the wild-type sequence as well as the Y100I and G121V mutant sequences as the basis of the library, five double mutants were identified from the screen, namely H12Y/Y100I (SEQ ID NO: 19), H12L/Y100I (SEQ ID NO: 20), R98H/F103S (SEQ ID NO: 21) M42T/H114R (SEQ ID NO: 22), and I61F/T68S (SEQ ID NO: 23).

Figure 19:
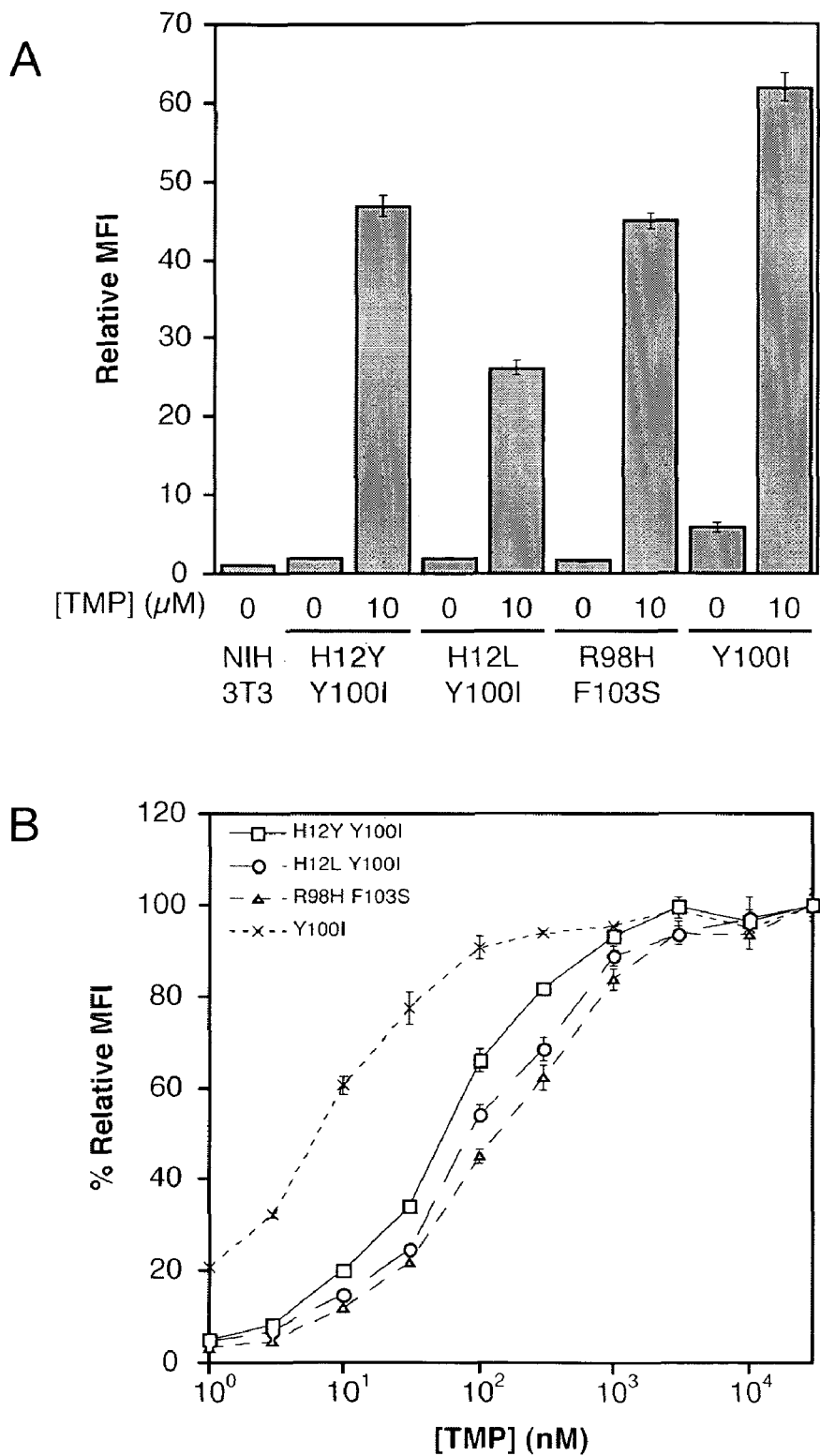
FIG. 19A is a graph showing the relative mean fluorescence intensity in cells harboring mutant DHFR-YFP fusion proteins in the absence and presence of ligand.
FIG. 19B shows the results of a dose response experiment, in which the cells expressing DHFR-YFP mutants were exposed to increasing amounts of ligand.

FIG. 19A shows the relative mean fluorescence intensity in cells harboring these mutant N-terminal fusion proteins in the absence and presence of ligand. While the Y100I mutant produced the greatest amount of stabilization, the difference between the levels of YFP in the absence and presence of ligand were greater with the each of the mutants H12Y/Y100I, H12L/Y100I, and R98H/F103S. FIG. 19B shows the results of a dose response experiment, in which cells harboring the same mutants as used in the experiment shown in FIG. 19A were exposed to increasing amounts of ligand. Consistent with this result shown in FIG. 19A, fusion proteins harboring the Y100I mutant are more stable in the presence of lower concentrations of ligand (or no ligand) but are no more stable in the presence of higher concentrations of ligand.

Figure 20:
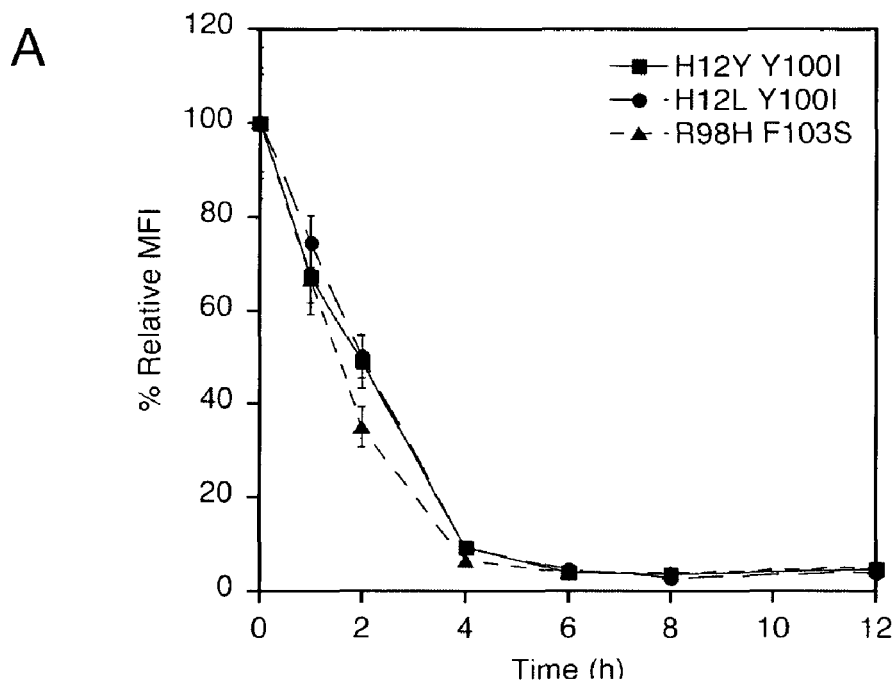
FIGS. 20A and 20B show the kinetics of decay and stabilization, respectively, of three DHFR mutants fused to the N-terminus of YFP.
Figure 20:
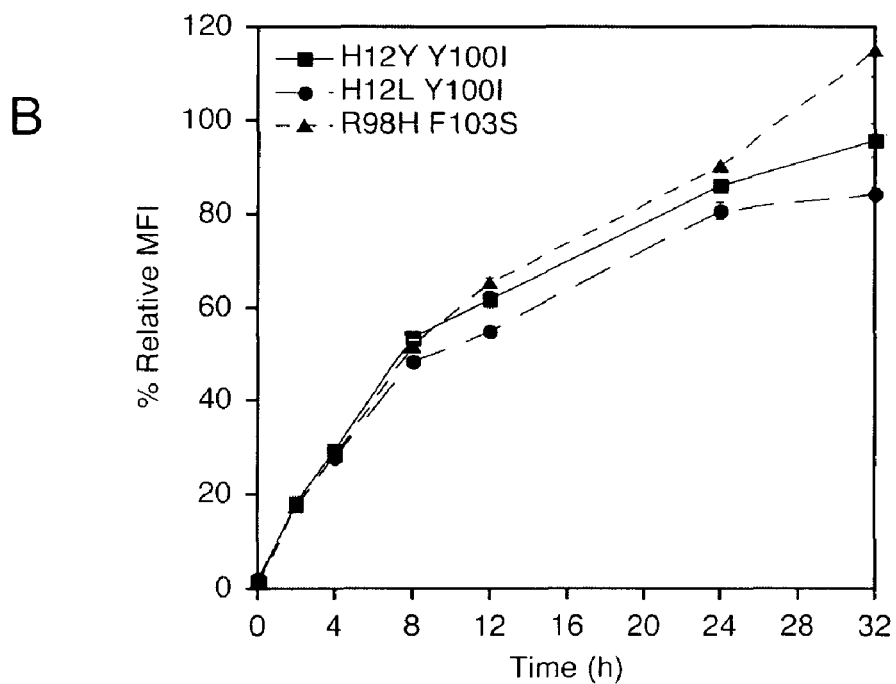

The kinetics of decay and stabilization of the N-terminal fusion proteins harboring the H12Y/Y100I, H12L/Y100I, and R98H/F103S mutants is shown in FIGS. 20A and 20B, respectively. The three fusion proteins behaved in a similar manner, although the maximum levels of the R98H/F103S fusion protein appeared to be higher than the others.

These results demonstrate that the DHFR-derived stability-affecting proteins can functions as in the context of either an N-terminal fusion or a C-terminal fusion with a POI.

5. Exemplary Systems for Conditionally Stabilizing Biological Macromolecules Ideal techniques for conditionally stabilizing biological macromolecules are specific, fast, reversible, and tunable. Cell-permeable small molecules often deliver the latter three features but, apart from a few well-known exceptions, cell-permeable small molecules are typically not specific for a single biological target. The ideal conditional stabilization technology combines the specificity of reverse genetics (i.e., well-defined DNA changes in a large genomic background) with the conditionality of cell-permeable small molecules.

Using small libraries of FKBP and DHFR variants (20,000 to 30,000 members) in combination with a convenient cell-based screening assay, several ligand stabilized destruction domains were identified, which conferred ligand-dependent stability to a POI. A list of proteins that have to date been stabilized using the methods and compositions described herein is provided in Example 12. The FKBP-derived destabilizing domains conferred ligand-dependent stability to cytoplasmic, nuclear, and a transmembrane protein, indicating that the present methods and compositions are generally applicable to the study of protein function. Stability, and therefore function, of the fusion proteins was greatly increased upon addition of a cell-permeable high-affinity ligand. For example, when the most destabilizing FKBP variants from the screen, i.e., FKBP L106P, was fused to YFP, the fusion protein is expressed at only ~1-2% of its maximum level in the absence of the stabilizing ligand. This fusion protein is fully stabilized upon the addition of 1 μM Shield1.

Variant and mutant FKBP proteins are exemplified by FKBP F36V (SEQ ID NO: 1) and the variants described in the text, Table 1 (N-terminal fusion proteins), and Table 2 (C-terminal fusion proteins). Exemplary variants have the substitutions F15S (SEQ ID NO: 2), V24A (SEQ ID NO: 3), H25R (SEQ ID NO: 4), E60G (SEQ ID NO: 5), L106P (SEQ ID NO: 6), D100G (SEQ ID NO: 7), M66T (SEQ ID NO: 8), R71G (SEQ ID NO: 9), D100N (SEQ ID NO: 10), E102G (SEQ ID NO: 11), and K105I (SEQ ID NO: 12). As tested, these variants include the F36V mutation (SEQ ID NO: 1); however, a similar mutation that accommodates a bulky side chain of a cell-permeable ligand is expected to produce similar results. Moreover, the methods allow for the screening of additional mutations that yield efficient single-ligand stabilized destruction domains.

A further mutant FKBP included additional amino acid sequence that altered the behavior of the protein such that it stabilized a POI in the absence of ligand and caused degradation of the PO1 in the presence of ligand. Thus the system can be used in a "drug-OFF" or "drug-ON" configuration. Such "drug-OFF" configurations may utilize a FKBP binding domain fused to a sequence substantially identical to that of SEQ ID NO:18.

The results obtained using DHFR variants suggests that Y100I (SEQ ID NO: 14) G121V (SEQ ID NO: 15) variants, particularly with the N18T/A19V (SEQ ID NO: 17) or F103L (SEQ ID NO: 16), H12Y/Y100I (SEQ ID NO: 19), H12L/Y100I (SEQ ID NO: 20), and R98H/F103S (SEQ ID NO: 21) substitutions, are well-suited for use as single-ligand stabilized destruction domain. However, the methods allow for the screening of additional mutations, including those for operation in a "drug-ON" configuration, as well as in the exemplified "drug-OFF" configuration.

The abundance of variants obtained in the screens, as well as the ability to use different ligand-binding domains, suggests that further refinements in screening may lead to additional stability-affecting proteins selected for various properties (e.g., rate of degradation, potency of stabilization, subcellular localization, and the like). Moreover, the stability-affecting proteins work when fused to either the N- or the C-terminus of a POI, illustrating the modularity of the components of the system.

The present systems work in different cell types, and work in cell culture and in animals. The system provides heretofore unprecedented control of the levels of preselected protein in cells, with excellent dose and temporal control. While the present methods have been described with reference to the FKBP and DHFR-derived destabilizing domains, other domains may be used. Preferred stability-affecting proteins modulate the degradation of a fusion protein, as determined, for example, using the kinetic and immunological assays described herein.

Preferred stability-affecting proteins produce a 5, 10, 20, 30, 40, 50, 60, or more-fold difference in the levels of a preselected protein that can be detected in cell or animals in the absence or presence of ligand. In some embodiments, the gene or allele encoding the naturally-occurring POI (i.e., the native protein, not a fusion protein) is deleted or disrupted in the genome of the cells or animal in which the conditional protein stability system is used or replaced by a DNA encoding the fusion protein. In this manner, the only source of the POI is the conditionally stabilized fusion protein, allowing its function to be studies in the absence of the interfering wild-type/naturally-occurring protein.

In some embodiments of the method, the strategy is "drug-ON," in that the stabilizing ligand must be present for stabilization of the fusion protein. However, if the POI exhibits a dominant negative phenotype, the system may be "drug-OFF," in that addition of the ligand stabilizes the dominant negative fusion protein, which in turn inhibits the function of its cellular target protein.

The stability-affecting proteins may encompass amino acid substitutions that do not substantially affect stability, including conservative and non-conservative substitutions Preferably, the amino acid sequences of the peptide inhibitors encompassed in the invention have at least about 60% identity, further at least about 70% identity, preferably at least about 75% or 80% identity, more preferably at least about 85% or 90% identity, and further preferably at least about 95% identity, to the amino acid sequences set forth herein. Percent identity may be determined, for example, by comparing sequence information using the advanced BLAST computer program, including version 2.2.9, available from the National Institutes of Health. The BLAST program is based on the alignment method of Karlin and Altschul ((1990) *Proc. Natl. Acad. Sci. U.S.A.* 87:2264-68) and as discussed in Altschul et al. ((1990) J. Mol. Biol. 215:403-10; Karlin and Altschul (1993) *Proc. Natl. Acad. Sci. U.S.A.* 90:5873-77; and Altschul et al. (1997) *Nucleic Acids Res.* 25:3389-3402).

Conservative amino acid substitutions may be made in the amino acid sequences described herein to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, amino acids having acidic side chains, such as aspartic acid and glutamic acid, can often be substituted with amino acids having amide side chains, such as asparagine and glutamine.

The stability-affecting proteins may be fragments of the above-described destabilizing domains, including fragments containing variant amino acid sequences. Such fragments are readily identified using the assays described herein. Preferred fragments retain the ability to bind to a stabilizing ligand with similar efficiency to the destabilizing domains described herein or with at least 90% efficiency, at least 80% efficiency, at least 70% efficiency, or even at least 50% efficiency with respect to the described stability-affecting proteins.

Stabilizing ligands for use according to the methods described herein are exemplified by SLF* (i.e., 1-[2-(3,4,5-trimethoxy-phenyl)-butyryl]-piperazine-2-carboxylic acid 1-(3-carboxymethoxy-phenyl)-3-(3,4-dimethoxy-phenyl)-propyl ester) and Shield1 (i.e., 1-[2-(3,4,5-trimethoxy-phenyl)-butyryl]-piperazine-2-carboxylic acid 3-(3,4-dimethoxy-phenyl)-1-[3-(2-morpholin-4-yl-ethoxy)-phenyl]-propyl ester), both shown in FIG. 1B, and MaRap (C20-methallylrapamycin). A feature of these FKBP ligands is that they contain a "bump" (i.e., a bulky side-chain substituent) that prevents the ligand from binding to wild-type (i.e., naturally-occurring) FRB domain of FRAP/mTor, thereby minimizing the biological effects associated with rapamycin administering. The "bump" in the ligand corresponds to a "hole" (i.e., a compensatory, cavity-forming substitution or mutation) in the FRB domain of FRAP/mTor.

Other stabilizing ligands may be used according to the present methods. Such ligands include rapamycin-derived ligands containing other bulky side-chains at positions of the molecule known to mediate binding to FKBP. As illustrated by the exemplary stabilizing ligands, the particular side-chain is not critical, with both aliphatic and aromatic side-chains producing acceptable results. Numerous other bulky R-groups are expected to give similar results, including but not limited to alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic groups. The R-groups may contain a hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and secondary or tertiary amine, (i.e., —NR'R" where each R' or R" is independently selected from hydrogen, alkyl, substituted alkyl, alkenyl, substituted alkenyl, cycloalkyl, substituted cycloalkyl, aryl, substituted aryl, heteroaryl, substituted heteroaryl, heterocyclic, substituted heterocyclic, etc.

A related aspect of the methods and compositions are cells transfected with nucleic acids encoding a fusion protein comprising a protein of interest fused in frame to a stability-affecting protein. Expression of the fusion protein may be driven by the endogenous promoter, ideally reproducing the spatial and temporal expression patterns of the unmodified gene. The cells may be transfected, e.g., using an expression vector, or transduced (i.e., infected) using a viral vector, including but not limited to a vector derived from a retrovirus (e.g., a lentivirus), herpesvirus, pox virus, adenovirus, adenoassociated virus, or an RNA virus, such as poliovirus, flavivirus, alphavirus, or the like. The exemplary viral vector was based on a retrovirus.

The system was shown to be effective eukaryotic cells, including mammalian cells and protozoan parasites; therefore, the system can be expected to work in various eukaryotic cells, including those of humans, primates, rodents, dogs, cats, horses, cows, sheep, insects, amphibians, and apicomplexan parasites. The cells may be in culture or in a living organism. As noted above, the wild-type or naturally-occurring gene or allele encoding the POI may be deleted to facilitate study of the conditionally stabilized POI.

The present methods and compositions also allow the creation of transgenic animals harboring engineered alleles that direct the expression of a ligand-stabilized POI. Expression of the fusion protein may be driven by the endogenous promoter, ideally reproducing the spatial and temporal expression patterns of the unmodified gene. The ligand may be administered regularly from an early age (including in utero) to stabilize the fusion protein until the mice achieve a specified age, at which time withdrawal of the ligand results in a the rapid degradation of the fusion protein. Unlike Cre-mediated gene disruption (see Background section), this method is reversible, simply by reinitiating the administration of the ligand, allowing the rapid, reversible, and conditional control of protein function in a complex system.

The ability to specifically and conditionally stabilize a POI in a cell will enable the study of many proteins to determine their biological function and importance in a cell. The present methods and composition represent a significant improvement over current methods of conditional protein regulation.

6. Kits of Parts

The methods and compositions described herein may be packaged together with instructions for use, as in a kit of parts. Preferred kits of parts include nucleic acids encoding stability-affecting proteins, one or more ligands, and instructions for use. The instructions may contain information relating the inserting (i.e., "cloning") a POI into a plasmid, in-frame with a stability-affecting protein. The instructions may also include dosing recommendations and hardware, such as syringes, to deliver the fusion protein to an organism or to cells.

EXAMPLES

The following examples are illustrative in nature and are in no way intended to be limiting. Examples relating to generating and screening stability-affecting proteins apply generally to FKBP, DHFR, and other polypeptides that can be used as stability-affecting proteins.

Example 1

FKBP Library Generation

Diversity in the FKBP sequence was generated using a combination of error-prone PCR and nucleotide analog mutagenesis. Primers for mutagenic PCR were designed to anneal upstream of the 5' restriction site to be used for cloning the mutagenesis products into the pBMN iHcRed-tandem retroviral expression vector and downstream of the 3' restriction site. Three independent condition sets were used to generate diversity. Condition set "A" utilized 4 ng template, 0.5 µM of each oligonucleotide primer, 5 units Taq polymerase, 5 mM $MgCl_2$, 0.2 mM $MnCl_2$, 0.4 mM dNTPs in equal ratio and an excess of 0.2 mM dATP and dCTP. Condition set "B" was identical to A except that dGTP and dTTP were present in excess. Condition set C utilized the non-natural nucleotides 8-oxo-dGTP and dPTP to encourage nucleotide misincorporation (Zaccolo et al., 1996). The FKBP libraries were pooled and ligated into the pBMN iHcRed-t retroviral expression vector, affording a library containing $\sim 3 \times 10^4$ members.

Example 2

FKBP Synthetic Ligands

SLF* and Shield1 were synthesized essentially as described (Holt et al., 1993; Yang et al., 2000).

Example 3

Cell Culture, Transfections, and Transductions

The NIH3T3 cell line was cultured in DMEM supplemented with 10% heat-inactivated donor bovine serum (Invitrogen), 2 mM glutamine, 100 U/ml penicillin and 100 μg/ml streptomycin. All other cell lines were cultured with 10% heat-inactivated fetal bovine serum (Invitrogen), 2 mM glutamine, 100 U/ml penicillin and 100 μg/ml streptomycin.

The ΦNX ecotropic packaging cell line was transfected using standard Lipofectamine 2000 protocols. Viral supernatants were harvested 48 hrs post-transfection, filtered and concentrated 10-fold using an Amicon Ultra centrifugal filter device (Millipore, 100-kDa cut-off). NIH3T3 cells were incubated with the concentrated retroviral supernatants supplemented with 4 μg/ml polybrene for 4 hrs at 37° C. Cells were washed once with PBS and cultured in growth media for 24-36 hrs to allow for viral integration, then assayed as described.

HeLa cells were plated at $7 \times 10^4$ cells per well of a 24-well plate 12 hours prior to transfection. Cells were transfected with either 200 ng Silencer® Lamin A/C siRNA (Ambion) or a negative control siRNA using the GeneSilencer protocol. Cell lysates were immunoblotted with an anti-lamin A/C antibody (Clone 14, BD Transduction Laboratories).

Example 4

Flow Cytometry

Twenty-four hours prior to analysis, transduced NIH3T3 cells were plated at $1 \times 10^5$ cells per well of a 12-well plate and treated as described. Cells were removed from the plate using PBS+2 mM EDTA, washed once with PBS, and resuspended in 200 μL PBS. Cells were analyzed at the Stanford Shared FACS Facility using FlasherII with 10,000 events represented.

Example 5

Protein-of-Interest Origin and Antibodies

Proteins tested as fusions to destabilizing domains were of the following origin, and the following antibodies were used for immunoblotting: Arf6 Q67L (human, 3A-1, Santa Cruz Biotechnology); Arl7 Q72L (human, BC001051, Protein Tech Group, Inc.); Cdc42 Q61L (human, P1, Santa Cruz Biotechnology); CD8α (mouse, 5H10, Caltag Laboratories); CDK1 (human, H-297, Santa Cruz Biotechnology); CREB (mouse, 86B10, Cell Signaling Technology); FKBP (human, 2C1-97, BD PharMingen); GSK-3β (mouse, 0011-A, Santa Cruz Biotechnology); Hsp90 (mouse, 68, BD Transduction Laboratories); p21 (human, H-164, Santa Cruz Biotechnology); Rac1 Q61L (human, C-11, Santa Cruz Biotechnology); RhoA Q63L (human, 26C4, Santa Cruz Biotechnology); Securin (human, Z23.YU, Zymed Laboratories); YFP, *Aequorea victoria* (JL-8, Clontech).

Example 6

Phalloidin Staining and Microscopy

NIH3T3 cells stably expressing constitutively active GTPases fused to destabilizing domains were treated with 1 μM Shield1 for 24 hr. At this time, cells were washed once with PBS, plated at $8 \times 10^3$ cells in 4-well LabTek Chambered coverglass (NUNC) coated with 1 mg/ml poly-D-lysine (Sigma), along with mock-treated transduced cells and transduced cells treated with 1 μM Shield1. Cells were cultured for 24 hr in 10% DBS, then cultured in serum-free media for 12 hr. Cells were then washed with PBS, fixed in 4% paraformaldehyde for 15 min, permeabilized in 0.2% Triton X-100 for 5 min, stained with 1 μg/ml Alexa Fluor 488-conjugated phalloidin (Invitrogen; A12379) in PBS for 20 min, and washed with PBS. Fixed cells were imaged using a Bio-Rad Radiance 2100 confocal microscope.

Example 7

Identification of Ligand-Responsive Destabilizing Domain

To identify FKBP variants (i.e., mutants) with a high affinity for the synthetic FKBP ligand SLF* (FIG. 1B) a cell-based screening assay was used in which a library based on the FKBP F36V gene sequence was generated using error-prone PCR, and then cloned in-frame in front of yellow fluorescent protein (YFP). Measurement of the fluorescence of YFP served as an indicator of FKBP stability.

A Moloney murine leukemia retroviral expression system was used to stably integrate this library of DNAs encoding FKBP-YFP fusion proteins into NIH3T3 fibroblasts. The transduced cells were subjected to three rounds of sorting using flow cytometry. In the first round, cells were treated with the FKBP ligand SLF* (5 μM, FIG. 1B) for 24 hours prior to sorting. The fluorescent cells were collected and further cultured in the absence of ligand for 60 hours. Reanalysis revealed that approximately 5% of the cell population exhibited decreased fluorescence levels, indicating that the majority of the sequences were either unmutated or contained mutations that did not affect stability of the fusion protein. This small population of cells exhibiting decreased fluorescence was collected and cultured again in the presence of SLF* (5 μM) for 24 hours, at which time YFP-expressing cells were collected and the genomic DNA was isolated. The sequence analysis of 72 FKBP-derived library clones (Table 1) revealed several frequently recurring mutations that were distributed fairly evenly over the primary amino acid sequence. All sequences maintained the F36V mutation. To validate the screening method and to further characterize the FKBP-derived ligand-responsive destabilizing domains, we chose five variants (F15S, V24A, H25R, E60G, and L106P) for further analysis.

TABLE 1

Shield 1-dependent N-terminal FKBP mutants isolated from library screen.

| Clone | No. mutations | Identity of mutations |
|---|---|---|
| 1-37 | 0 | none |
| 38 | 0 | stop codon introduced |
| 39 | 0 | dropped base |
| 40 | 0 | mixed sequence |
| 41 | 1 | F15S |
| 42 | 1 | F15S |
| 43 | 1 | V24A |
| 44 | 1 | K34R |
| 45 | 1 | S38P |
| 46 | 1 | F46L |
| 47 | 1 | V63F |
| 48 | 1 | M66V |
| 49 | 1 | R71S |
| 50 | 1 | P78T |

TABLE 1-continued

Shield 1-dependent N-terminal FKBP mutants isolated from library screen.

| Clone | No. Mutations | Identity of mutations |
|---|---|---|
| 51 | 1 | D79G |
| 52 | 1 | A81V |
| 53 | 1 | E102G |
| 54 | 1 | L106P |
| 55 | 2 | F15S, N43S |
| 56 | 2 | Y26H, Q53R |
| 57 | 2 | G28R, E31G |
| 58 | 2 | F48I, E60G |
| 59 | 2 | G51D, S77P |
| 60 | 2 | E54G, F99L |
| 61 | 2 | Q65R, L106P |
| 62 | 3 | V2A, L50A, L106A |
| 63 | 3 | T6A, V24A, I91A |
| 64 | 3 | Q3R, N43S, G69S |
| 65 | 3 | K44E, E60G, V63A |
| 66 | 3 | W59R, E60G, I76M |
| 67 | 4 | R13H, V24A, K35A, M49A |
| 68 | 6 | S8P, G28R, L30P, S39P, F99L, D100G |
| 69 | 7 | F15S, H25R, K47G, K73R, I76V, D79G, I90V |
| 70 | 10 | H25R, M29T, L30P, D32G, P45S, F48L, K52E, S67G, L104P, L106P |
| 71 | 11 | H25R, M29T, L30P, D32G, P45S, F48L, K52E, E54G, S67G, L104P, L106P |
| 72 | 16 | I7T, S8P, P9L, D11N, T14A, F15L, H25Y, L30P, D37N, D41N, A64T, I76M, G83D, T85A, I91V, F99V |

Example 8

Characterization of Ligand-Responsive Destabilizing Domain

The variant FKBP-derived, ligand-responsive destabilizing domains were assayed for stability in the presence and absence of a derivative of SLF* in which the carboxylic acid is replaced with a morpholine group (FIG. 1B). This functional group is commonly appended to drug-like molecules to improve their pharmacokinetic properties, and was added to SLF* at a position unlikely to interfere with FKBP binding. The modified SLF*-derived, cell-permeable FKBP ligand was designed to protect an otherwise unstable protein domain from degradation, and was therefore called Shield1 (Shield1).

Each variant FKBP-derived, ligand-responsive destabilizing domain was separately transduced into NIH3T3 cells, and YFP fluorescence levels were measured in the absence of Shield1 (FIG. 2A). All five mutants showed decreased fluorescence levels with respect to a positive control, indicating that the variants obtained from the library screen were destabilizing. The most destabilizing variation, L106P, produced YFP fluorescence at a level of only 1-2% relative to the positive control. All FKBP-derived, ligand-responsive destabilizing domain variants produced increased fluorescence signal when incubated in the presence of Shield1 (FIG. 2A). The difference in the efficiency of rescue (i.e., stabilization by Shield1) varied by over an order of magnitude, as shown in FIG. 2B. Variant V24A showed the most efficient rescue, with the extracellular concentration of Shield1 required to obtain 50% of the maximum YFP signal being 5 nM (i.e., $EC_{50}$~5 nM). The more destabilizing L106P variant required higher concentrations of Shield1 ($EC_{50}$~100 nM) to stabilize the YFP fusion protein.

In a kinetic study of NIH3T3 cells stably expressing each of the five FKBP-derived, ligand-responsive destabilizing domain variants, YFP fluorescence increased at approximately the same rate upon addition of Shield1, with maximum fluorescence achieved at 24 hours and stably maintained for at least an additional 48 hours without further addition of Shield1 (FIG. 2C). These results suggest that, upon addition of Shield1, these FKBP mutants are able to adopt a conformation that approximates the stability of the wild type protein, and that increases in fluorescence are mainly a function of the rate of protein synthesis and/or YFP maturation within the cell. In a related experiment, NIH3T3 cells transduced with the FKBP L106P-YFP fusion (hereafter L106P-YFP) were treated with various concentrations of Shield1 and YFP fluorescence was monitored as a function of time (FIG. 2C). YFP expression is observed within 15 min, and cells treated with lower concentrations of Shield1 reach steady state expression levels more rapidly than cells treated with higher concentrations of Shield1.

Upon withdrawal of Shield1, distinct differences in fluorescence decay profiles were observed among the FKBP-derived, ligand-responsive destabilizing domain variants (FIG. 2D), revealing a correlation between the rate of degradation and the degree of destabilization. Variant H25R, which is the least destabilizing of this group, showed the slowest rate of degradation, whereas L106P, the most destabilizing of the five, was degraded most quickly, with protein levels becoming negligible within four hours.

To correlate YFP fluorescence with intracellular protein levels and to look for evidence of partial proteolysis, cells stably expressing each destabilizing domain fused to YFP were either mock-treated or treated with Shield1. Cell lysates were prepared and used for immunoblot analysis along with antibodies specific for either FKBP (FIG. 2E) or YFP (data not shown). Neither antibody was capable of detecting protein in lysates from mock-treated cells, whereas the fusion protein was detected in Shield1-treated cells. Cells transformed with either the F15S or L106P variant were also examined using fluorescence microscopy, which demonstrated Shield1-dependent fluorescence (data not shown).

The mechanism of degradation was examined for the F15S and L106P variants. Since the ubiquitin-proteasome system is a major mediator of intracellular protein degradation (Pickart, 2004), the cells expressing either the FKBP-derived, ligand-responsive destabilizing domain variants F15S or L106P were incubated with MG132 (FIG. 2F) or lactacystin (FIG. 9), which inhibit ubiquitin-proteasome-mediated protein degradation. The inability of the cells to degrade the variant FKBP fusion proteins following the withdrawal of Shield1, indicating that degradation was mediated, at least in part, by the proteasome.

RNAi has become a widely used tool for reducing intracellular levels of a protein of interest. The rate of RNAi-mediated silencing of an endogenous gene was compared to the rate of degradation achieved through the fusion of a protein of interest to the above-described destabilizing domain. Lamin A/C is a non-essential cytoskeletal protein commonly used as a control in RNAi experiments. Previous studies have shown more than 90% reduction in lamin A/C expression in HeLa cells assayed 40 to 45 hours after transfection of the cells with a cognate siRNA duplex (Elbashir et al., 2001), which suggests that the half-life of the lamin A/C proteins is about 10-12 hours. This half-life is significantly shorter than that of YFB, which is 26 hrs (Corish and Tyler-Smith, 1999). HeLa cells transfected with siRNA against lamin A/C showed a decrease in protein levels after 24 hours, with a significant reduction in lamin A/C observed by 48 hours (FIG. 2G, FIG. 10). In contrast, cells stably expressing L106P-YFP show nearly complete degradation of the fusion within 4 hours of removal of Shield1. These results demonstrate that fusion of a destabilizing domain to a protein of interest dramatically reduces its stability in cultured cells, causing the protein of interest to be quickly degraded upon removal of the stabilizing ligand.

Example 9

Dose-Dependent Regulation of Intracellular Protein Levels

To determine the ability of the variant FKBP fusion proteins, in combination with Shield1, to modulate the levels of YFP in a dose-dependent manner, NIH3T3 cells stably expressing the L106P-YFP variant were exposed to different concentrations of Shield1 over the course of one week (FIG. 3). The smooth line (i.e., having no data points indicated by squares) are the predicted YFP levels based on the dose-response curve shown in FIG. 2B, as measured by flow cytometry.

Example 10

Identification and Characterization of C-Terminal Destabilizing Domains

A screen of a YFP-FKBP library (reversed compared to the previous orientation of FKBP and YFP) was performed to identify candidate C-terminal destabilizing domains (Table 2). Six FKBP variants (M66T, R71G, D100G, D100N, E102G, and K105I) were selected for further analysis. Overall, destabilizing domains fused to the C-terminus of YFP are less destabilizing than their N-terminal counterparts (Table 1). For example, when the L106P mutant is fused to the N-terminus of YFP (L106P-YFP), fluorescence is only ~1-2% of that observed in the presence of Shield1. However, when the orientation is reversed (YFP-L106P), fluorescence in the absence of Shield1 is ~10% of that observed in its presence.

TABLE 2

Shield1-dependent C-terminal FKBP mutants isolated from library screen.

| Clone | No. mutations | Identification of mutations |
|---|---|---|
| 1-5 | 0 | None |
| 6 | 0 | Stop codon introduced |
| 7-8 | 0 | Incomplete sequence |
| 8-12 | 0 | Mixed sequence |
| 13 | 1 | G1R |
| 14 | 1 | L30P |
| 15 | 1 | M66T |
| 16 | 1 | D100G |
| 17 | 1 | D100N |
| 18 | 1 | E102G |
| 19 | 1 | E102G |
| 20 | 1 | E107G |
| 21 | 2 | E5K, R71G |
| 22 | 2 | E5K, R71G |
| 23 | 2 | D11G, K73R |
| 24 | 2 | Q20L, T27A |
| 25 | 2 | T21A, H25R |
| 26 | 2 | C22F, M29T |
| 27 | 2 | M29T, D100G |
| 28 | 2 | E31G, E107G |
| 29 | 2 | K34Q, Q70R |
| 30 | 2 | S67G, Q70R |
| 31 | 2 | G89S, K105I |
| 32 | 3 | V4M, G33R, G58S |
| 33 | 3 | D11A, D32G, K44R |
| 34 | 3 | D11G, N43D, D79G |

TABLE 2-continued

Shield1-dependent C-terminal FKBP mutants isolated from library screen.

| Clone | No. mutations | Identification of mutations |
|---|---|---|
| 35 | 3 | D11G, R13C, F48L |
| 36 | 3 | G19D, K35R, K105E |
| 37 | 3 | E31G, R71G, K105E |
| 38 | 3 | K35R, G69S, I76V |
| 39 | 3 | E61G, H94R, K105R |
| 40 | 3 | D79G, P93S, D100R |
| 41 | 3 | D79G, P93S, D100R |
| 42 | 4 | T6A, I7T, T14I, M66V |
| 43 | 4 | T21A, N43D, A72V, E107G |
| 44 | 4 | M29T, E31K, K52R, T75A |
| 45 | 4 | R42G, K52R, D79G, E107G |
| 46 | 5 | I7T, M29V, F48L, T85A, K105R |
| 47 | 7 | Q3R, F15S, T21A, K44E, K73E, P88T, K105R |
| 48 | 8 | T6S, P9S, M29V, K34R, R42G, Q53R, K73R, D79G |

Figure 11:
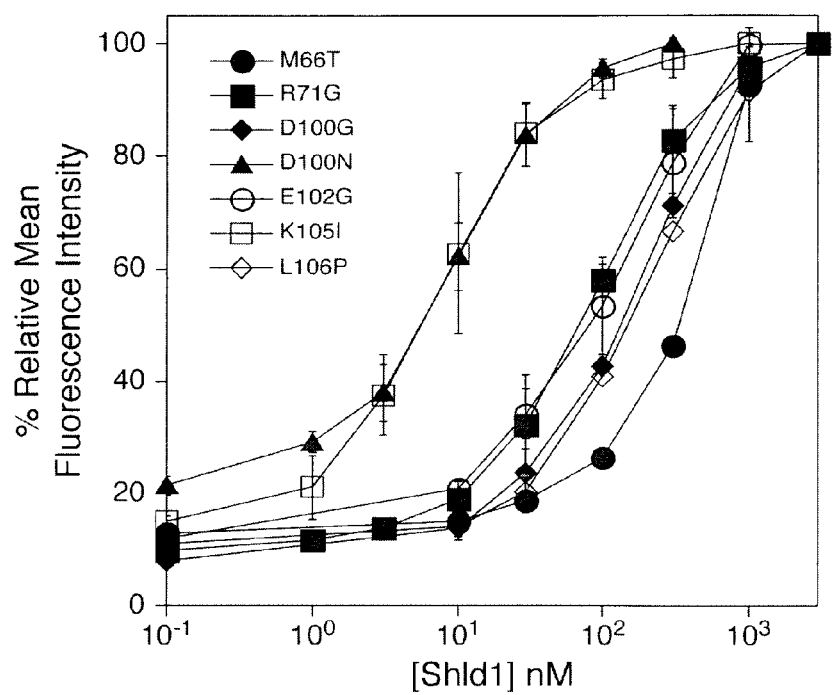
FIG. 11 is a graph showing the levels of fluorescence of various YFP-FKBP fusion proteins (i.e., C-terminal FKBP mutants) in response to different concentrations of Shield1. NIH3T3 cells stably expressing YFP-FKBP fusion proteins were incubated with three-fold dilutions of Shield1 (3 μM to 0.1 nM) and fluorescence was monitored by flow cytometry. The data are presented as MFI±SEM relative to that of the maximum fluorescence intensity observed for the individual variant. The experiment was performed in triplicate.

Nonetheless, C-terminal destabilizing domains respond to Shield1 in a dose-dependent manner comparable to N-terminal destabilizing domains, with $EC_{50}$ values ranging from 10 nM to 100 nM (FIG. 11). As observed with N-terminal destabilizing domains, all variants exhibit nearly identical rates of increase in fluorescence upon addition of Shield1, regardless of the degree of instability conferred (not shown).

Example 11

Ligand-Dependent Stability in Multiple Cells Lines

Destabilizing domains fused to either the N- or C-terminus of YFP were also transfected into several different cells lines, i.e., NIH3T3, HEK 293T, HeLa, and COS-1 cells, to assess the behavior of the FKBP-derived, ligand-responsive destabilizing domain variants in different cells. Shield1-dependent fluorescence was observed in all cell lines (Table 3), demonstrating that ligand-dependent stability is not restricted to one cell type. The FKBP-derived destabilizing domains can be stabilized using Shield1 as well as the commercially available ligand, FK506 (FIG. 13). However, unlike Shield1, FK506 perturbs the cellular environment by inhibiting calcineurin.

TABLE 3

Fluorescence of FKBP-YFP fusions (N- terminal or C-terminal) in transiently transfected cell lines in the absence of Shield1.

| | % Residual YFP Fluorescence* | | | |
|---|---|---|---|---|
| | FKBP-YFP | | YFP-FKBP | |
| | F15S | L106P | D100G | L106P |
| NIH3T3 | 7 | 8 | 16 | 16 |
| HEK 293T | 7 | 5 | 15 | 19 |
| HeLa | 8 | 6 | 9 | 12 |
| COS-1 | 12 | 19 | 22 | 26 |

*Data are presented as the average mean fluorescence intensity relative to that of the maximum fluorescence intensity observed for the individual mutant. The experiment was performed in duplicate.

Example 12

Ligand-Dependent Stability for a Variety of Proteins

To show that FKBP variants are efficient in destabilizing proteins other than YFP, the F15S and L106P variants were fused at the N-termini, to the kinases GSK-3β and CDK1, the cell cycle regulatory proteins securin and p21, and three small GTPases, Rac1, RhoA and Cdc42 (FIG. 4A). All the fusion proteins demonstrated Shield1-dependent stability, as was the case for YFP. The absence of Shield1 resulted in the degradation of CDK1 (an otherwise stable protein) as well as p21 and securing (cell cycle regulators with relatively short half-lives; Nigg, 2001). Shield1-dependent stability of fusion proteins containing the D100G or L106P destabilizing domain variants fused to the C-terminus of the transcription factor CREB, or the small GTPases, Arf6 and Arl7, (FIG. 4B), was also observed. To date, about 20 fusion proteins have been tested and all demonstrate ligand-dependent stability (Table 4). An additional example is CD8α, a transmembrane glycoprotein found on the surface of T cells, which was able to be detected on the surface of cells by flow cytometry (FIG. 5), in a Shield1-dependent manner. As shown in FIG. 5, the destabilizing FKBP variants D100G and L106P also conferred Shield1-dependent stability to a transmembrane protein, CD8α, when fused at the C-terminus of the transmembrane protein. Here, NIH3T3 cells stably expressing the fusion proteins were divided into three pools (groups). The first group (−) was mock-treated, the second group (+) was treated with 1 μM Shield1 for 24 hrs, and the third group (+/−) was treated with 1 μM Shield1 for 24 hrs, and then washed with media and cultured for 24 hr in the absence of Shield1. Live cells were then probed with a FITC-conjugated anti-CD8α antibody and assayed by flow cytometry. Data are presented as the average mean fluorescence intensity±SEM from an experiment performed in triplicate.

TABLE 4

| | Proteins destabilized by FKBP Destruction Domains |
|---|---|
| 1 | yellow fluorescent protein (YFP) |
| 2 | glycogen synthase kinase-3β |
| 3 | securin |
| 4 | p21$^{WAF/CIP}$ |
| 5 | Rac1 |
| 6 | Cdc42 |
| 7 | RhoA |
| 8 | cAMP response element binding transcription factor (CREB) |
| 9 | cyclin-dependent kinase 1 (CDK1) |
| 10 | Arf6 |
| 11 | Arl7 |
| 12 | cyclin B1 |

TABLE 4-continued

| | Proteins destabilized by FKBP Destruction Domains |
|---|---|
| 13 | firefly luciferase |
| 14 | Oct3/4 |
| 15 | Sox2 |
| 16 | Nanog |
| 17 | c-Myc |
| 18 | Klf4 |
| 19 | Aid |
| 20 | Apobec1 |

Example 13

Ligand-Dependent Control of Cellular Phenotypes

Expression of constitutively active small GTPases causes well-characterized changes in cellular morphology (Heo and Meyer, 2003). To determine if FKBP-derived destabilizing domains, in combination with Shield1, could affect cell morphology by modulating GTPases levels, several small GTPases (i.e., RhoA, Cdc42, or Arl7) were fused to the destabilizing domains (FIGS. 4A and 4B). NIH3T3 cells were individually transduced with the L106P-RhoA, L106P-Cdc42, or Arl7-L106P (note arrangement of fusions), and then mock-treated or treated with Shield1, and visualized using confocal microscopy (not shown). Shield 1-treated cells displayed the predicted morphologies, i.e., expression of RhoA induced the formation of stress fibers, expression of Cdc42 resulted in filopodia formation, and expression of Arl7 induced the shrunken cell phenotype (Heo and Meyer, 2003). Mock treatment with Shield1 produced cells with fibroblast-like morphologies. These GTPase-dependent morphology changes were reversible, as treatment with Shield1 followed by removal of Shield1 also produced cells with fibroblast-like morphologies. The penetrance of the observed phenotype was high, with a large percentage of cells (>90%) exposed to a given experimental condition displaying the predicted behavior (not shown).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A conditional protein stability system, comprising:
a nucleic acid sequence encoding a fusion protein that includes a protein of interest fused in-frame to a single-polypeptide chain, ligand-dependent, stability-affecting protein that is derived from a naturally-occurring ligand binding protein and is a variant FKBP having an F36V amino acid substitution in addition to one or more amino acid substitutions selected from the group consisting of F15S, V24A, H25R, E60G, L106P, D100G, M66T, R71G, D100N, E102G, and K105I, and
a ligand that binds to the stability-affecting protein to modulate its stability, wherein the ligand is Shield1, wherein upon introduction of the nucleic acid sequence to a cell, the fusion protein is expressed, and wherein the fusion protein is stabilized in the presence of the ligand.

2. The system of claim 1, wherein the ligand preferentially binds to the stability-affecting protein compared to the naturally-occurring ligand-binding protein.

3. A kit of parts comprising the system of claim 1 along with instructions for use.

* * * * *

UNITED STATES PATENT AND TRADEMARK OFFICE
CERTIFICATE OF CORRECTION

PATENT NO. : 8,173,792 B2
APPLICATION NO. : 12/069235
DATED : May 8, 2012
INVENTOR(S) : Wandless et al.

Page 1 of 1

It is certified that error appears in the above-identified patent and that said Letters Patent is hereby corrected as shown below:

In the Specification:

Column 1, line 14 thereof: change "This work was supported in part by National Institutes of Health grants (GM068589 and GM073046). Accordingly, the United States government has certain rights in this invention." to --This invention was made with Government support under contracts GM068589 and GM073046 awarded by the National Institutes of Health. The Government has certain rights in the invention.--

Signed and Sealed this
Twenty-first Day of April, 2015

Michelle K. Lee
*Director of the United States Patent and Trademark Office*